United States Patent
Herr et al.

(10) Patent No.: US 9,110,057 B2
(45) Date of Patent: *Aug. 18, 2015

(54) MULTI-DIRECTIONAL MICROFLUIDIC DEVICES AND METHODS

(75) Inventors: Amy E. Herr, Oakland, CA (US); Mei He, Albany, CA (US); Chenlu Hou, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 13/055,679

(22) PCT Filed: May 18, 2010

(86) PCT No.: PCT/US2010/035314
§ 371 (c)(1),
(2), (4) Date: Apr. 8, 2011

(87) PCT Pub. No.: WO2010/135364
PCT Pub. Date: Nov. 25, 2010

(65) Prior Publication Data
US 2011/0177618 A1 Jul. 21, 2011

Related U.S. Application Data

(60) Provisional application No. 61/179,649, filed on May 19, 2009, provisional application No. 61/257,361, filed on Nov. 2, 2009.

(51) Int. Cl.
*B01L 3/00* (2006.01)
*G01N 33/543* (2006.01)
*G01N 33/53* (2006.01)

(52) U.S. Cl.
CPC .... *G01N 33/54386* (2013.01); *B01L 3/502761* (2013.01); *G01N 33/5302* (2013.01);
(Continued)

(58) Field of Classification Search
None
See application file for complete search history.

(56) References Cited

U.S. PATENT DOCUMENTS 5,407,546 A * 4/1995 Schickle ............... 204/459
5,420,016 A 5/1995 Boguslaski et al.
(Continued)

FOREIGN PATENT DOCUMENTS

JP 2004-61319 A 2/2004
JP 2006-10529 A 1/2006
(Continued)

OTHER PUBLICATIONS

He et al., "Automated microfluidic protein immunoblotting", Nature Protocols, vol. 5, No. 11, pp. 1844-1856 (2010).
(Continued)

*Primary Examiner* — Melanie Y Brown
*Assistant Examiner* — Rebecca Martinez
(74) *Attorney, Agent, or Firm* — Rudy J. Ng; Bret E. Field; Bozicevic, Field & Francis LLP

(57) ABSTRACT

Multi-directional microfluidic devices and methods for using the same are provided. Aspects of the invention include microfluidic devices that are configured to subject a sample to two or more directionally distinct flow fields, and include a separation medium and a binding medium, where the binding medium is in fluid communication with the separation medium. Also provided are methods of using the devices as well as systems and kits that include the devices. The devices, systems and methods find use in a variety of different applications, including diagnostic and validation assays.

26 Claims, 21 Drawing Sheets

(52) U.S. Cl.
CPC .... *B01L2200/0652* (2013.01); *B01L 2300/069* (2013.01); *B01L 2300/0816* (2013.01); *B01L 2400/0421* (2013.01)

(56) References Cited

U.S. PATENT DOCUMENTS

| | | | |
|---|---|---|---|
| 5,637,469 | A | 6/1997 | Wilding et al. |
| 5,858,195 | A | 1/1999 | Ramsey |
| 6,499,499 | B2 | 12/2002 | Dantsker et al. |
| 6,613,581 | B1 | 9/2003 | Wada et al. |
| 6,818,112 | B2 | 11/2004 | Schneider et al. |
| 6,969,452 | B2 | 11/2005 | He et al. |
| 6,974,526 | B2 | 12/2005 | Lee et al. |
| 7,112,444 | B2 | 9/2006 | Beebe et al. |
| 7,235,389 | B2 | 6/2007 | Lim et al. |
| 7,241,421 | B2 | 7/2007 | Webster et al. |
| 7,641,780 | B2 | 1/2010 | Lee et al. |
| 7,754,150 | B2 | 7/2010 | Wada et al. |
| 8,329,016 | B1 | 12/2012 | Sommer et al. |
| 2001/0041332 | A1 | 11/2001 | Hillebrand et al. |
| 2002/0153046 | A1 | 10/2002 | Dantsker et al. |
| 2003/0089605 | A1 | 5/2003 | Timperman |
| 2003/0127331 | A1* | 7/2003 | Leka ............................ 204/466 |
| 2004/0112751 | A1 | 6/2004 | Han et al. |
| 2004/0158890 | A1 | 8/2004 | Thomashow et al. |
| 2004/0209354 | A1 | 10/2004 | Mathies et al. |
| 2005/0020814 | A1 | 1/2005 | Rudolph et al. |
| 2005/0106740 | A1* | 5/2005 | Boyes et al. ..................... 436/86 |
| 2005/0155861 | A1 | 7/2005 | Guzman et al. |
| 2005/0217996 | A1 | 10/2005 | Liu et al. |
| 2005/0269267 | A1 | 12/2005 | Patton et al. |
| 2006/0191792 | A1 | 8/2006 | Herr et al. |
| 2006/0211055 | A1 | 9/2006 | Hafeman et al. |
| 2007/0121111 | A1* | 5/2007 | Blumenfeld et al. ......... 356/318 |
| 2007/0131552 | A1 | 6/2007 | Jung et al. |
| 2009/0071828 | A1 | 3/2009 | Squires et al. |
| 2009/0194483 | A1 | 8/2009 | Robotti et al. |
| 2010/0108519 | A1 | 5/2010 | Soper et al. |
| 2011/0177618 | A1 | 7/2011 | Herr et al. |

FOREIGN PATENT DOCUMENTS

| | | | |
|---|---|---|---|
| JP | 2007-518977 | A | 7/2007 |
| JP | 2008-537119 | A | 9/2008 |
| WO | WO 00/73799 | A1 | 12/2000 |
| WO | WO 02/086332 | A1 | 10/2002 |
| WO | WO2006/102516 | * | 9/2006 |
| WO | 2010135364 | | 11/2010 |
| WO | 2011106693 | A2 | 9/2011 |
| WO | 2011142781 | | 11/2011 |
| WO | 2012071472 | A2 | 5/2012 |
| WO | 2012075308 | A2 | 6/2012 |

OTHER PUBLICATIONS

He et al., "Polyacrylamide Gel Photopatterning Enables Automated Protein Immunoblotting in a Two-Dimensional Microdevice", J. Am. Chem. Soc., vol. 132, pp. 2512-2513 (2010).

Subramanian, "Dye-ligand affinity chromatography: the interaction of cibacron blue F3Ga with proteins and enzymes", Critical Reviews in Biochemistry and Molecular Biology, vol. 16, No. 2, pp. 169-205 (1984).

Fonslow et al. 'Free-Flow Electrophoresis on an Anodically Bonded Glass Microchip' Anal. Chem., Sep. 1, 2005, vol. 77(17), pp. 5706-5710.

He et al., 'Microfluidic Polyacrylamide Gel Electrophoresis with in Situ Immunoblotting for Native Protein Analysis' Anal Chem, 2009, vol. 81, pp. 8177-8184.

Lerch et al., 'Electrokinetic Fluid Control in Two-Dimensional Planar Microfluidic Devices' Anal. Chem., Aug. 25, 2007, vol. 79(19), pp. 7485-7491.

Renzi, et al. 'Hand-held microanalytical instrument for chip-based electrophoretic separations of proteins' Anal Chem., Jan. 15, 2005, vol. 77(2), pp. 435-441.

Song, et al. 'Electrophoretic concentration of proteins at laser-patterned nanoporous membranes in microchips.' Anal Chem., Aug. 1, 2004, vol. 76(15), pp. 4589-4592.

Zeng et al., 'Microfluidic Self-patterning of Large-Scale Crystalline Nanoarrays for High-Throughput Continuous DNA Fractionation' Angew. Chem. Int. Ed., Jul. 15, 2008, vol. 47, pp. 6388-6391.

Renzi, et al. Hand-held microanalytical instrument for chip-based electrophoretic separations of proteins. Anal Chem. Jan. 15, 2005;77(2):435-41.

Song, et al. Electrophoretic concentration of proteins at laser-patterned nanoporous membranes in microchips. Anal Chem. Aug. 1, 2004;76(15):4589-92.

Kim et al., "Microfluidic Western Blotting: Cationic Surfactant Based Protein Sizing Integrated with Electrostatic Immobilization", IEEE MEMS 24th International Conference, pp. 197-200 (2011).

Office Action dated Jul. 8, 2014 issued in corresponding Japanese Patent Application No. 2012-511973.

Zhang et al., "High-Speed Free-Flow Electrophoresis on Chip", Anal. Chem., vol. 75, pp. 5759-5766 (2003).

* cited by examiner

MULTI-DIRECTIONAL MICROFLUIDIC DEVICES AND METHODS

CROSS-REFERENCE TO RELATED APPLICATIONS

Pursuant to 35 U.S.C. §119(e), this application claims priority to the filing date of U.S. Provisional Patent Application Ser. No. 61/179,649, filed May 19, 2009, and U.S. Provisional Application Ser. No. 61/257,361, filed Nov. 2, 2009, which applications are incorporated herein by reference in their entirety.

REFERENCE TO GOVERNMENT SUPPORT

This invention was made in part with government support under a grant from the National Institutes of Health, grant number NIDCR 5U01 DE014961. The government has certain rights in this invention.

INTRODUCTION

A variety of analytical techniques may be used to detect specific analytes in a given sample. For example, Western blotting can be used to detect proteins in a sample by using gel electrophoresis to separate the proteins in the sample followed by probing with antibodies specific for the target protein. Southern blotting combines transfer of electrophoresis-separated DNA fragments to a filter membrane and subsequent fragment detection by probe hybridization. Northern blotting involves the use of electrophoresis to separate RNA samples by size, and detection with a hybridization probe complementary to part of or the entire target sequence. Eastern blotting can be used to detect protein post translational modifications (PTM) by analyzing electrophoresis-separated proteins for post-translational modifications using probes specific for lipids, carbohydrate, phosphorylation or any other protein modifications. Far-Western blotting is similar to Western blotting, but uses a non-antibody protein to bind the protein of interest, and thus can be used to detect protein-protein interactions. Southwestern blotting is a technique that can be used to detect DNA-binding proteins by using gel electrophoresis to separate the proteins in a sample followed by probing with genomic DNA fragments.

Conventional blotting techniques, as discussed above, may fall short of performance needs for applications that demand either high-throughput sample analysis or operation in resource poor settings. Blotting techniques may require labor-intensive, time consuming, multi-step procedures carried out by a trained technician, and thus may be impractical for use in a clinical setting.

SUMMARY

Multi-directional microfluidic devices and methods for using the same are provided. Aspects of the invention include microfluidic devices that are configured to subject a sample to two or more directionally distinct flow fields, and include a separation medium and a binding medium, where the binding medium is in fluid communication with the separation medium. Also provided are methods of using the devices as well as systems and kits that include the devices. The devices, systems and methods find use in a variety of different applications, including diagnostic and validation assays.

DETAILED DESCRIPTION

Figure 1:
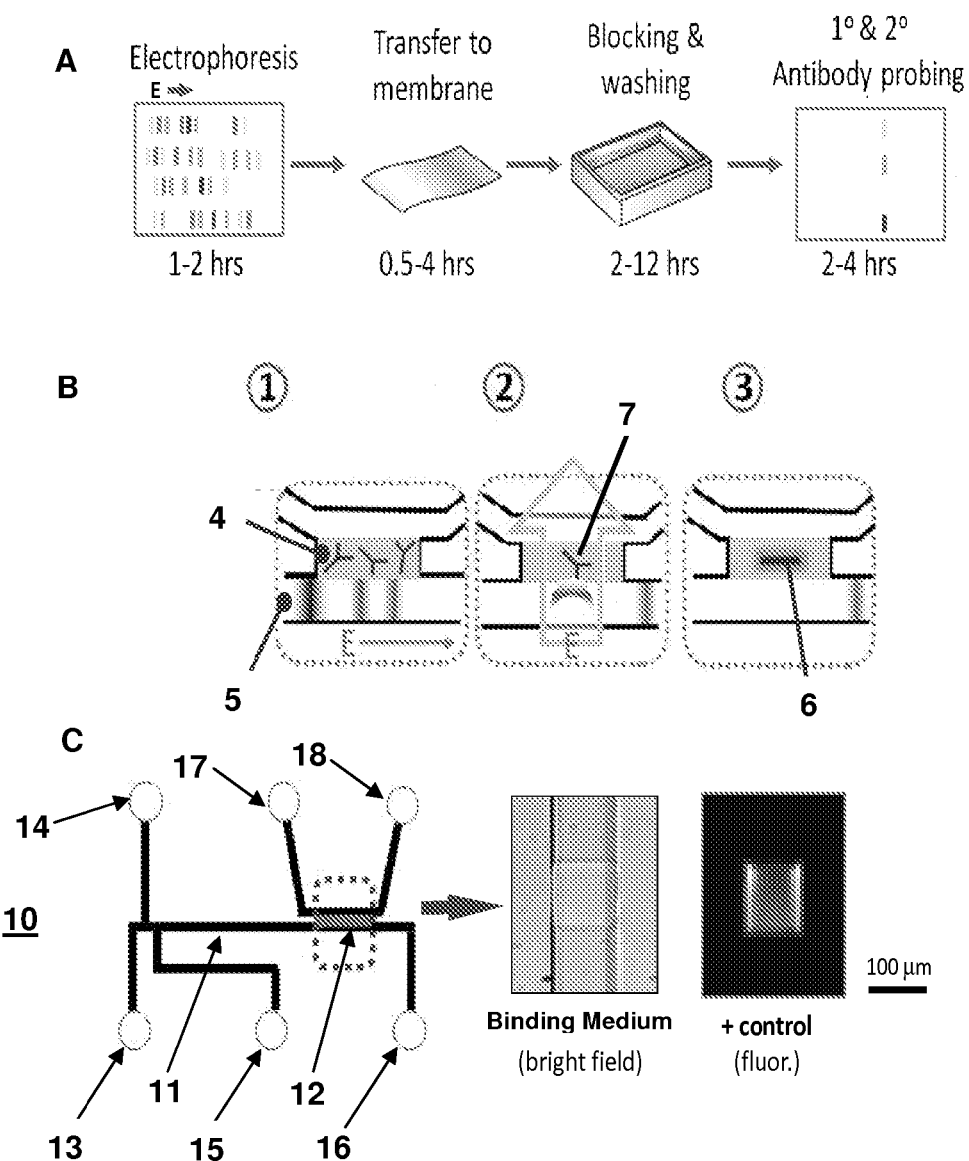
FIG. 1A shows a schematic of a conventional immunoblotting procedure.
FIG. 1B shows a schematic of a method for detecting the presence of an analyte in a sample according to embodiments of the present disclosure.
FIG. 1C shows a schematic of a microfluidic device and bright field and fluorescence images of a binding medium within a microfluidic device according to embodiments of the present disclosure.

Multi-directional microfluidic devices and methods for using the same are provided. Aspects of the invention include microfluidic devices that are configured to subject a sample to two or more directionally distinct electric fields, and include a separation medium and a binding medium, where the binding medium is in fluid communication with the separation medium. Also provided are methods of using the devices as well as systems and kits that include the devices. The devices, systems and methods find use in a variety of different applications, including diagnostic and validation assays.

Aspects of the present disclosure include a microfluidic device for detecting an analyte in a fluid sample and configured to subject a sample to two or more directionally distinct flow fields, where the microfluidic device includes: a separation medium having a separation flow path with a first directional axis; and a binding medium having a labeling flow path with a second directional axis, where the binding medium is in fluid communication with the separation medium.

In certain embodiments, the separation medium includes a polymeric gel. In some cases, the binding medium includes a binding member stably associated with a support. In some instances, the support includes a membrane. In some instances, the support includes a polymeric gel. Certain embodiments of the microfluidic devices include a binding member that includes a protein or a binding fragment thereof. For instances, the protein may be an antibody. In some cases, the analyte includes a fluorescent label.

In certain embodiments, the second directional axis is orthogonal to the first directional axis. In some instances, the microfluidic device includes a chamber containing the separation medium and the binding medium.

Aspects of the present disclosure also include a method of detecting an analyte in a fluid sample. The method includes: introducing the fluid sample into a microfluidic device configured to subject a sample to two or more directionally distinct flow fields; directing the sample through the separation medium to produce a separated sample; and detecting the analyte in the separated sample. As described above, the microfluidic device includes: a separation medium having a separation flow path with a first directional axis; and a binding medium having a labeling flow path with a second directional axis, where the binding medium is in fluid communication with the separation medium.

In certain embodiments, the method includes transferring the separated sample to the binding medium. In other embodiments, the method includes transferring a binding member to the separated sample. In some instances, the method further includes concentrating the sample prior to directing the sample through the separation medium to produce a separated sample.

Embodiments of the subject methods include that the method is a diagnostic method. In addition, in some cases, the method is a validation method.

Aspects of the present disclosure additionally include a system for detecting an analyte in a fluid sample. The system includes a microfluidic device as described herein, and a detector. As described above, the microfluidic device is configured to subject a sample to two or more directionally distinct flow fields, where the microfluidic device includes: a separation medium having a separation flow path with a first directional axis; and a binding medium having a labeling flow path with a second directional axis, wherein the binding medium is in fluid communication with the separation medium.

In certain embodiments, the detector is a photomultiplier tube (PMT), a charge-coupled device (CCD), an intensified charge-coupled device (ICCD), a complementary metal-oxide-semiconductor (CMOS) sensor, a visual colorimetric readout, or a photodiode. In some instances, the system further includes microfluidic components configured to direct a fluid through the microfluidic device.

Aspects of the present disclosure additionally include a kit that includes a microfluidic device as described herein, and a buffer. As described above, the microfluidic device includes: a separation medium having a separation flow path with a first directional axis; and a binding medium having a labeling flow path with a second directional axis, where the binding medium is in fluid communication with the separation medium.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Embodiments of the present disclosure include multi-directional microfluidic devices. By "multi-directional" is meant more than one direction, such as two or more directions, three or more directions, four or more directions, etc. In certain embodiments, two or more directions are included in a single plane, such that the two or more directions are co-planar. In some instances, the two or more directions are not co-planar, such that two directions are included in different, intersecting planes. In these cases, the two or more directions may be multi-dimensional. By "multi-dimensional" is meant more than one dimension, such as two-dimensional, three-dimensional, and the like. Directions that are multi-dimensional may occupy a region of three-dimensional space. For example, two directions that are not co-planar may each be included in different, intersecting planes, such that the intersecting planes that include the two directions occupy a region of three-dimensional space.

In certain embodiments, the microfluidic devices are configured to direct a fluid in more than one direction (e.g., the microfluidic devices are multi-directional), such as two or more directions, three or more directions, four or more directions, etc. For example, the microfluidic devices may be configured to direct a fluid in two directions, three directions, four directions, etc. In some instances, the microfluidic devices are multi-dimensional. For example, the microfluidic devices may be configured to direct a fluid in two or more directions, where the two or more directions are not co-planar, such that the two or more directions are included in two or more different, intersecting planes. In these cases, the intersecting planes that include the two or more directions may occupy a region of three-dimensional space. For instance, the microfluidic devices may be included in a substrate, such that the microfluidic device is planar. The microfluidic device may be configured to direct fluids in multiple directions within that plane. In certain embodiments, the microfluidic devices are configured to direct a fluid in multiple dimensions, such as three dimensions. For example, the microfluidic device may be configured to direct a fluid in multiple directions within the same plane, as well as direct a fluid in non-coplanar directions, such that the microfluidic device is configured to be a three-dimensional microfluidic device.

In certain embodiments, the microfluidic devices include a separation medium. The separation medium may be configured to separate the analytes in a sample from each other. In some cases, the separation medium is configured to separate the analytes in a sample based on the physical properties of the analytes. For example, the separation medium may be configured to separate the analytes in the sample based on the molecular weight, size, charge (e.g., charge to mass ratio), isoelectric point, etc. of the analytes. In certain instances, the separation medium is configured to separate the analytes in the sample based on the molecular weight of the analytes. In some cases, the separation medium is configured to separate the analytes in the sample based on the isoelectric point of the analytes (e.g., isoelectric point focusing). The separation medium may be configured to separate the analytes in the sample into distinct detectable bands of analytes. By "band" is meant a distinct detectable region where the concentration of an analyte is significantly higher than the surrounding regions. Each band of analyte may include a single analyte or several analytes, where each analyte in a single band of analytes has substantially similar physical properties, as described above.

In certain embodiments, the separation medium is configured to separate the analytes in a sample as the sample traverses the separation medium. In some cases, the separation medium is configured to separate the analytes in the sample as the sample flows through the separation medium. Aspects of the separation medium include that the separation medium has a flow path with a directional axis. By "flow path" is meant the direction a fluid sample travels as it moves. In some instances, the flow path is the direction the sample travels as the sample traverses a medium, such as a separation medium, a binding medium, and the like. As indicated above, the separation medium may have a flow path with a directional axis. In some embodiments, the directional axis of the separation flow path is aligned with the length of the separation medium. In these embodiments, the sample traverses the separation medium in the direction of the separation flow path of the separation medium (e.g., the sample may traverse the separation medium along the length of the separation medium). In some cases, the length of the separation medium is greater than the width of the separation medium, such as 2 times, 3 times, 4 times, 5 times, 10 times, 20 times, 50 times, 100 times, etc. the width of the separation medium. In some instances, the separation flow path of the separation medium is defined by a channel, such as a microfluidic channel. The separation medium may be included in a microfluidic channel, such that a sample traverses the separation medium as the sample flows through the microfluidic channel.

In certain embodiments, the separation medium includes a polymer, such as a polymeric gel. The polymeric gel may be a gel suitable for gel electrophoresis. The polymeric gel may include, but is not limited to, a polyacrylamide gel, an agarose gel, and the like. The resolution of the separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular weight differences of 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content of ranging from 1% to 20%, such as from 3% to 15%, including from 5% to 10%.

In some instances, the microfluidic devices include a concentration medium positioned upstream from the separation medium. By "upstream" is meant positioned proximal to a source of a fluid flow. The concentration medium may be configured to concentrate the sample prior to the sample contacting the separation medium. The concentration medium may include a polymeric gel, such as a polymeric gel with a small pore size. For example, the concentration medium may include a polyacrylamide gel that has a total acrylamide content of ranging from 5% to 10%, such as from 5% to 9%, including from 5% to 8%, or from 5% to 7%. In some instances, the concentration medium has a total polyacrylamide content of 6%. In certain embodiments, the concentration medium includes a membrane, such as a size exclusion membrane. The small pore size of the concentration medium may slow the electrophoretic movement of the sample through the concentration medium, thus concentrating the sample before it contacts the separation medium. In some instances, the concentration membrane is configured to increase the concentration of the sample by 2 times or more, 4 times or more, 10 times or more, 25 times or more, 50 times or more, 100 times or more, 500 times or more, 1000 times or more, 2500 times or more, etc.

In certain embodiments, the subject microfluidic devices include a binding medium positioned downstream from the separation medium. By "downstream" is meant positioned distal to a source of a fluid flow. The binding medium may have a labeling flow path with a directional axis. In some instances, the labeling flow path is the direction the sample travels as the sample or analyte traverses the binding medium. The sample or analyte may traverse the binding medium in the direction of the labeling flow path of the binding medium (e.g., the sample may traverse the separation medium along the directional axis of the binding medium). The binding medium may have a directional axis the same as, or different from the directional axis of the separation medium. For example, the separation medium may have a first directional axis and the binding medium may have a second directional axis. The first directional axis may be aligned in the same direction as the second directional axis. In some cases, the first directional axis is aligned in a different direction as the second directional axis. In cases where the first directional axis is aligned in a different direction as the second directional axis, the microfluidic devices are multi-dimensional (e.g., multi-directional) microfluidic devices, as described above. For example, the second directional axis may be at an angle of 180 degrees or less with respect to the first directional axis, such as 150 degrees of less, 135 degrees or less, including 120 degrees or less, 90 degrees or less, 60 degrees or less, 45 degrees or less, or 30 degrees or less with respect to the first directional axis. In certain embodiments, the second directional axis is orthogonal to the first directional axis.

In certain cases, the binding medium includes a polymer, such as a polymeric gel or polymeric monolith. By monolith is meant a single, contiguous structure. Monoliths may include a single region with the same physical and chemical composition, or may include two or more regions that differ in terms of their physical and chemical compositions. The polymeric gel may be a gel suitable for gel electrophoresis. The polymeric gel may include, but is not limited to, a polyacrylamide gel, an agarose gel, and the like. In some cases, the binding medium may include a polyacrylamide gel that has a total acrylamide content of ranging from 1% to 20%, such as from 3% to 15%, including from 5% to 10%. The polymeric monolith may be a monolith suitable for chromatography. The polymeric monolith may include, but is not limited to, acrylate polymers, alkylacrylate polymers, alkyl alkylacrylate polymers, copolymers thereof, and the like. In some instances, the binding medium includes a membrane. The membrane may include a nitrocellulose membrane, a polymer membrane, and the like. In some instances, the binding medium includes beads. The beads may include nitrocellulose beads, polymeric beads, combinations thereof, and the like.

In certain embodiments, the binding medium may be configured to bind to and retain an analyte of interest. In some instances, an analyte bound to the binding medium facilitates detection of the analyte. For example, the binding medium may include a binding member stably associated with a support. By "stably associated" is meant that a moiety is bound to or otherwise associated with another moiety or structure under standard conditions. In certain instances, the support is a polymeric gel or a membrane, as described above. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In certain embodiments, the binding member may be covalently bound to the support, such as cross-linked or copolymerized to the support. Covalent bonds between the binding member and the support include covalent bonds that involve reactive groups, such as, but not limited to, the following: glutaraldehyde, which utilizes the bifunctional linker glutaraldehyde to form covalent bonds with the amino/amide groups of both the binding member and the support; glycidyl methacrylate, which utilizes the glycidyl functional group (i.e., the epoxy functional group) for covalent bonding to the binding member and the methacrylate group for binding to the support; 4-nitrophenyl methacrylate, which can be used to acylate amine groups of the binding member to covalently bind to the support; N-hydroxysuccinimidyl acrylate (NHS-acrylate), which utilizes the N-hydroxysuccinimidyl group to interact with amino groups on the binding member for incorporation into the support.

A binding member can be any molecule that specifically binds to a protein or nucleic acid sequence or biomacromolecule that is being targeted (e.g., the analyte of interest). Depending on the nature of the analyte, binding members can be, but are not limited to, (a) single strands of DNA complementary to a unique region of the target DNA or RNA sequence for the detection of nucleic acids; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

In certain embodiments, the binding member includes an antibody. The binding member antibody may specifically bind to an analyte of interest. In some cases, the binding member is stably associated with a support, as described above. The support-bound binding member may be configured to specifically bind to the analyte of interest. As such, specific binding of the analyte of interest to the support-bound binding member may indirectly bind the analyte of interest to the support. Binding of the analyte of interest to the support may stably associate the analyte with the support and thus facilitate detection of the analyte of interest.

In certain embodiments, two or more different binding members are stably associated with the binding medium. The two or more different binding members may specifically bind to the same or different analytes. In some cases, the two or more different binding members may specifically bind to the same analyte. For instance, the two or more different binding members may include different antibodies specific for different epitopes on the same analyte. In other cases, the two or more different binding members may specifically bind to different analytes. For example, the two or more binding members may include different antibodies specific for epitopes on different analytes.

Aspects of the microfluidic devices include embodiments where the separation medium is in fluid communication with the binding medium. In certain embodiments, the binding medium is arranged downstream from the separation medium. The microfluidic device may be configured to direct the sample through the separation medium first to produce a separated sample. In some instances, the separation medium and the binding medium are in fluid communication with each other but are not in direct physical contact with each other. For instance, the separation medium may be in fluid communication with a channel or another medium, which in turn is in fluid communication with the binding medium. In certain embodiments, the microfluidic device is configured such that the separation medium and the binding medium are in direct fluid communication with each other. For example, the separation medium may be in direct contact with the binding medium. In some cases, the separation medium and the binding medium are bound to each other, such as co-polymerized. Embodiments where the separation medium is in direct fluid communication with the binding medium may facilitate the transfer of moieties from the separation medium to the binding medium or transfer of moieties from the binding medium to the separation medium with a minimal loss of moieties. In some instances, the microfluidic devices are configured such that moieties are quantitatively transferred from one medium to another (e.g., from the separation medium to the binding medium, or from the binding medium to the separation medium).

In certain embodiments, the microfluidic device is configured to direct the separated sample through the binding medium. In some instances, the microfluidic devices are configured such that the sample or analyte traverses from the separation medium to an intervening channel or medium and then traverses to the binding medium. In other cases, the microfluidic device is configured such that the separation medium and the binding medium are in direct fluid communication with each other, such that a sample or analyte can traverse directly from the separation medium to the binding medium. As described above, the binding medium may include binding members configured to bind to an analyte for detection of an analyte of interest in the separated sample.

In certain cases, the binding medium includes binding members that are not bound to the binding medium. For example, the binding medium may include binding members suspended or dissolved in a fluid, such as a buffer. In these cases, the device is configured to direct the binding members from the binding medium towards the separation medium. For example, the device may be configured to direct the binding members from the binding medium towards the separation flow path of the separation medium. As described above, the binding members may be configured to bind to an analyte for detection of an analyte of interest in the separated sample. In some instances, the microfluidic devices are configured such that the binding members traverse from the binding medium to an intervening channel or medium and then traverse to the separation medium. In other cases, the microfluidic device is configured such that the binding medium and the separation medium are in direct fluid communication with each other, such that a binding member can traverse directly from the binding medium to the separation medium.

In some instances, the microfluidic device is configured to subject a sample to two or more directionally distinct flow fields. By "flow field" is meant a region where moieties traverse the region in substantially the same direction. For example, a flow field may include a region where mobile moieties move through a medium in substantially the same direction. A flow field may include a medium, such as a separation medium, a binding medium, a loading medium, etc., where moieties, such as buffers, analytes, reagents, etc., move through the medium in substantially the same direction. A flow field may be induced by an applied electric field, a pressure differential, electroosmosis, and the like. In some embodiments, the two or more flow fields may be directionally distinct. For example, a first flow field may be aligned with the directional axis of the separation flow path of the separation medium. The first flow field may be configured to direct the sample or analytes through the separation medium along the separation flow path. A second flow field may be aligned with the directional axis of the labeling flow path of the binding medium. In some instances, the second flow field is configured to direct the sample or analytes through the binding medium along the labeling flow path. The second flow field may be configured to direct the sample or analytes through the binding medium such that the analyte of interest contacts its specific binding member. In some instances, the second flow field is configured to direct a binding member through the binding medium along the labeling flow path. The second flow field may be configured to direct the binding member through the binding medium such that the binding member contacts its specific analyte of interest. As described above, in certain instances, the directional axis of the labeling flow path is orthogonal to the directional axis of the separation flow path. In these instances, the second flow field may be orthogonal to the first flow field.

In certain embodiments, the microfluidic device is configured to subject a sample to two or more directionally distinct electric fields. The electric fields may facilitate the movement of the sample through the microfluidic device (e.g., electrokinetic transfer of the sample from one region of the microfluidic device to another region of the microfluidic device). The electric fields may also facilitate the separation of the analytes in the sample by electrophoresis (e.g., polyacrylamide gel electrophoresis (PAGE)), as described above. For instance, the electric field may be configured to direct the analytes in a sample through the separation medium of the microfluidic device. The electric field may be configured to facilitate the separation of the analytes in a sample based on the physical properties of the analytes. For example, the electric field may be configured to facilitate the separation of the analytes in the sample based on the molecular weight, size, charge (e.g., charge to mass ratio), isoelectric point, etc. of the analytes. In certain instances, the electric field is configured to facilitate the separation of the analytes in the sample based on the molecular weight of the analytes. In some cases, the electric field is configured to facilitate the separation of the analytes in the sample based on the isoelectric point of the analytes.

In some embodiments, the two or more electric fields may be directionally distinct. For example, a first electric field may be aligned with the directional axis of the separation flow path of the separation medium. The first electric field may be configured to direct the sample or analytes through the separation medium along the separation flow path. A second electric field may be aligned with the directional axis of the labeling flow path of the binding medium. In some instances, the second electric field is configured to direct the sample or analytes through the binding medium along the labeling flow path. The second electric field may be configured to direct the sample or analytes through the binding medium such that the analyte of interest contacts it specific binding member. In some instances, the second electric field is configured to direct a binding member through the binding medium along the labeling flow path. The second electric field may be configured to direct the binding member through the binding medium such that the binding member contacts its specific analyte of interest. As described above, in certain instances, the directional axis of the labeling flow path is orthogonal to the directional axis of the separation flow path. In these instances, the second electric field may be orthogonal to the first electric field.

In certain embodiments, the microfluidic device includes one or more electric field generators configured to generate an electric field. The electric field generator may be configured to apply an electric field to various regions of the microfluidic device, such as one or more of the separation medium, the binding medium, the loading medium, and the like. The electric field generators may be configured to electrokinetically transport the analytes and moieties in a sample through the various media in the microfluidic device. In certain instances, the electric field generators may be proximal to the microfluidic device, such as arranged on the microfluidic device. In some cases, the electric field generators are positioned a distance from the microfluidic device. For example, the electric field generators may be incorporated into a system for detecting an analyte, as described in more detail below.

Aspects of the microfluidic devices include a transfer flow path. The transfer flow path may be in fluid communication with the labeling flow path of the binding medium. For instance, the transfer flow path may be positioned downstream from the binding flow path. As described above, the binding medium may include a binding member that specifically binds to an analyte of interest. Moieties not of interest are not bound by the binding member and may traverse the binding medium without binding to the binding member. In certain embodiments, the transfer flow path is configured to direct moieties not of interest away from the binding medium. For example, the transfer flow path may be configured to direct moieties not of interest that traverse the binding medium without binding to the binding member away from the binding medium. In certain embodiments, the transfer flow path is configured to direct moieties through or to chemical or physical treatments in the binding medium. For example, resolved analytes may be driven through chemical denaturants, refolding chemicals, detergents, etc.

In some cases, the downstream end of the transfer flow path is in fluid communication with a waste reservoir, such that the transfer flow path is configured to direct the moieties not of interest to the waste reservoir. In some cases, the downstream end of the transfer flow path is in fluid communication with a secondary analysis device, such that the transfer flow path is configured to direct the moieties that pass through the binding medium without binding to the binding member to the secondary analysis device for further characterization of the moieties. The secondary analysis device may include, but is not limited to, a UV spectrometer, and IR spectrometer, a mass spectrometer, an HPLC, an affinity assay device, and the like. In some instances, the secondary analysis device is included on the same substrate as the microfluidic device. In these embodiments, the microfluidic device and the secondary analysis device may be provided on a single substrate for the analysis of a sample by one or more different analysis techniques. In certain embodiments, the secondary analysis device is included as part of a system, where the system includes a microfluidic device and one or more separate secondary analysis devices. As described above, the microfluidic device and the secondary analysis device may be in fluid communication with each other, such that moieties that pass through the microfluidic device may be directed to the secondary analysis device for further characterization of the moieties.

Figure 7A:
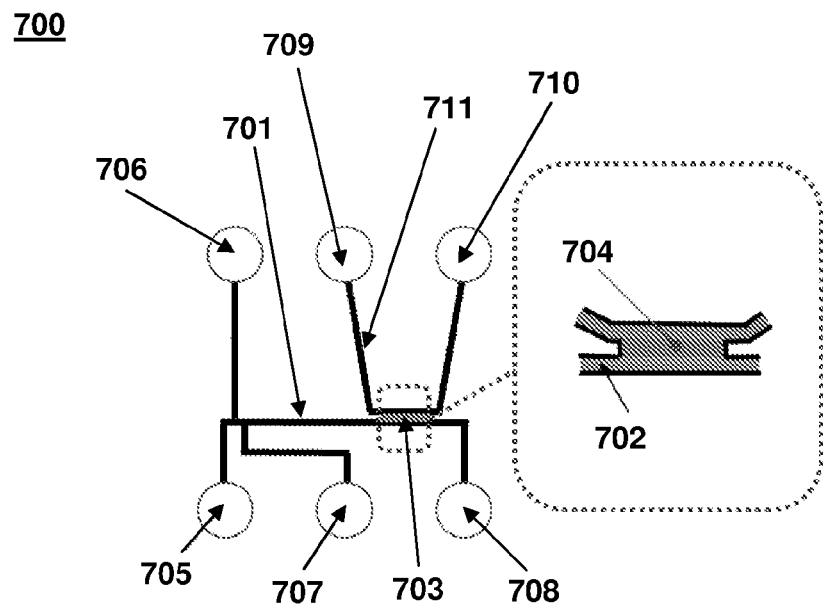
FIG. 7A shows a schematic of a microfluidic device according to embodiments of the present disclosure.

In some aspects, the separation and binding media are provided in different lengths of separate channels, as illustrated in FIGS. 1C and 7A. In these embodiments, the microfluidic devices are configured to include microfluidic channels in fluid communication with each other. The microfluidic channels may be elongated channels where the length of the channel is greater than the width of the channel. For example, the length of the microfluidic channel may be greater than the width of the microfluidic channel, such as 2 times, 3 times, 4 times, 5 times, 10 times, 20 times, 50 times, 100 times, etc. the width of the microfluidic channel.

The microfluidic devices may include a separation channel that includes a separation medium, as described above. The microfluidic devices may include a binding channel that includes a binding medium, as described above. In some instances, the separation channel is in fluid communication with the binding channel, such that the separation medium in the separation channel is in fluid communication with the binding medium in the binding channel. Some embodiments of the microfluidic devices include a separation channel and a binding channel, where the separation channel has a first directional axis and the binding channel has a second directional axis. The first directional axis and the second directional axis may be aligned in the same direction as each other or may be aligned in different directions from each other. For example, the directional axis of the separation channel may be at an angle of 180 degrees or less with respect to the binding channel, such as 150 degrees of less, 135 degrees or less, including 120 degrees or less, 90 degrees or less, 60 degrees or less, 45 degrees or less, or 30 degrees or less with respect to the binding channel. In certain embodiments, the directional axis of the binding channel is orthogonal to the directional axis of the separation channel.

Embodiments of the microfluidic channels may be made of any suitable material that is compatible with the microfluidic devices and compatible with the samples, buffers, reagents, etc. used in the microfluidic devices. In some cases, the microfluidic channels are made of a material that is inert (e.g., does not degrade or react) with respect to the samples, buffers, reagents, etc. used in the subject microfluidic devices and methods. For instance, the microfluidic channels may be made of materials, such as, but not limited to, glass, quartz, polymers, elastomers, paper, combinations thereof, and the like.

In certain embodiments, the microfluidic channels have a width ranging from 1 µm to 500 µm, such as from 5 µm to 300 µm, including from 10 µm to 200 µm, for example from 50 µm to 150 µm. In some instances, the microfluidic channels have a width of 100 µm. In certain embodiments, the microfluidic channels have a depth ranging from 1 µm to 200 µm, such as from 5 µm to 100 µm, including from 10 µm to 50 µm. In some cases, the microfluidic channels have a depth of 25 µm.

In some instances, the microfluidic devices include one or more sample input ports. The sample input port may be configured to allow a sample to be introduced into the microfluidic device. The sample input port may be in fluid communication with the separation medium. In some instances, the sample input port is in fluid communication with the upstream end of the separation medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

FIG. 1C shows a schematic of a microfluidic device 10. The microfluidic device 10 includes a separation medium 11 in fluid communication with a binding medium 12. The microfluidic device 10 also includes various inlets and outlets, such as fluid inlet 13, waste outlet 14, sample inlet 15, fluid outlet 16, fluid inlet 17, and fluid outlet 18. Fluid outlet 16 may be configured to direct separated analytes to a waste reservoir or to downstream secondary analysis devices, as desired. Similarly, fluid outlet 18 may be configured to direct unbound analytes to a waste reservoir or to downstream secondary analysis devices, as desired. FIG. 1C also shows bright field and fluorescence images of a binding medium within a microfluidic device.

FIG. 7A also shows a schematic of a microfluidic device 700 that includes microfluidic channels in fluid communication with each other, as described above. The microfluidic device 700 includes a separation channel 701 that includes a separation medium 702. The separation channel is in fluid communication with a binding channel 703 that includes a binding medium 704. The microfluidic device 700 may also include various inlets and outlets, such as, but not limited to the following: fluid inlet 705, which may be configured to direct a fluid into the microfluidic device 700; waste outlet 706, which may be configured to direct waste fluids away from the microfluidic device 700; sample inlet 707, which may be configured to direct a sample into the microfluidic device 700 upstream from the separation medium; fluid outlet 708, which may be configured to direct separated analytes that were not transferred to the binding channel 703 to a waste reservoir or to downstream secondary analysis devices, as desired; fluid inlet 709, which may be configured to direct a fluid to transfer channel 711; and fluid outlet 710, which may be configured to direct unbound analytes to a waste reservoir or to downstream secondary analysis devices, as desired.

In some aspects, the separation and binding media are provided in a single common chamber, as illustrated in FIGS. 12-16. In these embodiments, the microfluidic devices include a chamber. The chamber may include a separation medium and a binding medium. As described above, the separation medium may be in fluid communication, such as in direct physical contact, with the binding medium. In some cases, the separation medium is bound to the binding medium, such as copolymerized or cross-linked to the binding medium. As such, the chamber may be configured to contain both the separation medium and the binding medium in fluid communication with each other. The chamber may be configured to contain the separation medium and the binding medium such that the separation flow path of the separation medium is upstream from the labeling flow path of the binding medium.

In addition to the separation medium and the binding medium, the chamber may also include a loading medium. The loading medium may be in fluid communication with the separation medium. In some instances, the loading medium is in direct physical contact with the separation medium. For example, the loading medium may be bound to the separation medium, such as cross-linked or copolymerized with the separation medium. The loading medium may be positioned upstream from the separation medium, such that the sample contacts the loading medium before contacting the separation medium. In certain embodiments, the loading medium facilitates contacting a sample with the separation medium. For instance, the loading medium may be configured to concentrate the sample before the sample contacts the separation medium. In certain embodiments, the loading medium may include two or more regions that have different physical and/or chemical properties. The loading medium may include a loading region and a stacking region. The loading medium may be configured to include a loading region upstream from a stacking region.

In certain embodiments, the loading medium includes a polymer, such as a polymeric gel. The polymeric gel may be a gel suitable for gel electrophoresis. The polymeric gel may include, but is not limited to, a polyacrylamide gel, an agarose gel, and the like. In some cases, the loading region includes a polymeric gel with a large pore size. For example, the loading region may include a polyacrylamide gel that has a total acrylamide content of 5% or less, such as 4% or less, including 3% or less, or 2% or less. In some instances, the loading region has a total polyacrylamide content of 3%. In some cases, the stacking region of the loading medium may be configured to concentrate the sample before the sample contacts the separation medium. The stacking region may include a polymeric gel with a small pore size. For example, the stacking region may include a polyacrylamide gel that has a total acrylamide content of ranging from 5% to 10%, such as from 5% to 9%, including from 5% to 8%, or from 5% to 7%. In some instances, the stacking region has a total polyacrylamide content of 6%. The small pore size of the stacking region may slow the electrophoretic movement of the sample through the stacking region, thus concentrating the sample before it contacts the separation medium.

In certain instances, the chamber contains the loading medium, the separation medium and the binding medium. The chamber may be configured to contain the loading medium, the separation medium and the binding medium such that the loading medium, the separation medium and the binding medium are in fluid communication with each other, as described above. For example, the chamber may include a contiguous polymeric gel with various regions. Each region of the contiguous polymeric gel may have different physical and/or chemical properties. The contiguous polymeric gel may include a first region having a loading medium, a second region having a separation medium and a third region having a binding medium. The flow paths of each region of the polymeric gel may be configured such that a sample first contacts the loading medium, then contacts the separation medium, and finally contacts the binding medium.

In certain embodiments, the polymeric gel has a width ranging from 0.1 mm to 5 mm, such as from 0.2 mm to 2.5 mm, including from 0.5 mm to 1.5 mm. In some cases, the polymeric gel has a width of 1.0 mm. In some instances, the polymeric gel has a length ranging from 0.5 mm to 5 mm, such as from 0.5 mm to 3 mm, including from 1 mm to 2 mm. In certain instances, the polymeric gel has a length of 1.5 mm. In certain embodiments, the first region of the polymeric gel that includes the loading medium has a width ranging from 0.1 mm to 5 mm, such as from 0.2 mm to 2.5 mm, including from 0.5 mm to 1.5 mm. In some cases, the first region of the polymeric gel that includes the loading medium has a width of 0.9 mm. In some cases, the first region of the polymeric gel that includes the loading medium has a length ranging from 0.1 mm to 2 mm, such as from 0.1 mm to 1 mm, including from 0.1 mm to 0.5 mm. In certain embodiments, the first region of the polymeric gel that includes the loading medium has a length of 0.2 mm. In certain instances, the second region of the polymeric gel that includes the separation medium has a width ranging from 0.1 mm to 5 mm, such as from 0.2 mm to 2.5 mm, including from 0.5 mm to 1.5 mm. In some cases, the second region of the polymeric gel that includes the separation medium has a width of 0.9 mm. In some cases, the second region of the polymeric gel that includes the separation medium has a length ranging from 0.5 mm to 5 mm, such as from 0.5 mm to 3 mm, including from 1 mm to 2 mm. In certain embodiments, the second region of the polymeric gel that includes the separation medium has a length of 1.3 mm. In certain instances, the third region of the polymeric gel that includes the binding medium has a width ranging from 0.01 mm to 2 mm, such as from 0.01 mm to 1 mm, including from 0.05 mm to 0.5 mm. In some cases, the third region of the polymeric gel that includes the bonding medium has a width of 0.1 mm. In some cases, the third region of the polymeric gel that includes the binding medium has a length ranging from 0.5 mm to 5 mm, such as from 0.5 mm to 3 mm, including from 1 mm to 2 mm. In certain embodiments, the third region of the polymeric gel that includes the binding medium has a length of 1.5 mm.

In certain embodiments, the microfluidic device has a width ranging from 10 cm to 1 mm, such as from 5 cm to 5 mm, including from 1 cm to 5 mm. In some instances, the microfluidic has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

In certain embodiments, the microfluidic device is substantially transparent. By "transparent" is meant that a substance allows visible light to pass through the substance. In some embodiments, a transparent microfluidic device facilitates detection of analytes bound to the binding medium, for example analytes that include a detectable label, such as a fluorescent label. In some cases, the microfluidic device is substantially opaque. By "opaque" is meant that a substance does not allow visible light to pass through the substance. In certain instances, an opaque microfluidic device may facilitate the analysis of analytes that are sensitive to light, such as analytes that react or degrade in the presence of light.

Methods

Embodiments of the methods are directed to determining whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In certain embodiments, the microfluidic devices are configured to detect the presence of one or more analytes in a sample. Samples that may be assayed with the subject microfluidic devices may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular weight, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In some embodiments, the analyte of interest can be identified so that the presence of the analyte of interest can then be detected. Analytes may be identified by any of the methods described herein. For example, the analyte may include a detectable label. Detectable labels include, but are not limited to, fluorescent labels, colorimetric labels, chemiluminescent labels, enzyme-linked reagents, multicolor reagents, avidin-streptavidin associated detection reagents, non-visible detectable labels (e.g., radiolabels, gold particles, magnetic labels, electrical readouts, density signals, etc.), and the like. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethyl-benzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl) phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5'''-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino)naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-1-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In certain embodiments, the method includes introducing a fluid sample into a microfluidic device. Introducing the fluid sample into the microfluidic device may include directing the sample through a separation medium to produce a separated sample. In some cases, the separated sample is produced by gel electrophoresis as the sample traverses the separation medium, as described above. The separated sample may include distinct detectable bands of analytes, where each band includes one or more analytes that have substantially similar properties, such as molecular weight, size, charge (e.g., charge to mass ratio), isoelectric point, etc. depending on the type of gel electrophoresis performed.

Aspects of the methods may also include transferring the separated sample to a binding medium. Specific bands of analytes in the separated sample may be selectively transferred to the binding medium. In some cases, the method includes contacting an analyte of interest with a binding member in the binding medium. The binding member may specifically bind to the analyte, thus retaining the analyte in the binding medium. Moieties not of interest are not specifically bound by the binding members in the binding medium.

In certain embodiments, the method includes detecting analyte bound to the binding medium. Detectable binding of an analyte of interest to the binding members in the binding medium indicates the presence of the analyte of interest in the sample. Moieties not of interest that traverse the binding medium and do not bind to the binding members in the binding medium may be washed away or transferred to a secondary analysis device such as, but is not limited to, a UV spectrometer, and IR spectrometer, a mass spectrometer, an HPLC, an affinity assay device, and the like.

In certain embodiments, the method includes transferring a binding member from to the separated sample. Binding members may be transferred from the binding medium to specific bands of analytes in the separated sample. In some instances, the method includes contacting the binding member with an analyte of interest in the separated sample. In some cases, method includes stably associating the separated sample with the separation medium. For example, the method may include binding the separated sample to the separation medium. The separated sample may be chemically or physically bound to the separation medium, such as by contacting the separated sample with chemical reagents, cross-linking the separated sample to the separation medium, and the like. The binding member may specifically bind to an analyte or interest, thus retaining the binding member in the separation medium where the bound binding members may be subsequently detected. Binding members that do not specifically bind to analytes in the separated sample may be transferred through the separation medium.

In some cases, false-positive signals due to non-specific binding of the binding member to moieties not of interest are minimized. For example, non-specific binding of the binding member to other moieties not of interest may be minimized and the moieties not of interest will not be detected. The moieties not of interest may traverse through the binding medium without binding to the binding member. Thus, the binding member may specifically bind only to the analyte of interest. Specific binding of the binding member to only the analyte of interest may facilitate the specific detection of the analyte of interest in complex samples.

In certain embodiments, the method includes concentrating, diluting, or buffer exchanging the sample prior to directing the sample through the separation medium. Concentrating the sample may include contacting the sample with a concentration medium prior to contacting the sample with the separation medium. As described above, the concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes transferring moieties that are not bound by the binding members in the binding medium away from the binding medium. The unbound moieties may be directed to a transfer flow path that is in fluid communication with the labeling flow path of the binding medium. In some cases, the method includes transferring the unbound moieties to a waste reservoir. In other cases, the method includes directing the unbound moieties downstream from the binding medium for secondary analysis with a secondary analysis device such as, but is not limited to, a UV spectrometer, and IR spectrometer, a mass spectrometer, an HPLC, an affinity assay device, and the like.

Embodiments of the method may also include releasing the analyte bound to the binding medium. The releasing may include contacting the bound analyte with a releasing agent. The releasing agent may be configured to disrupt the binding interaction between the analyte and the binding member. In some cases, the releasing agent is a reagent, buffer, or the like, that disrupts the binding interaction between the analyte and the binding member causing the binding member to release the analyte. After releasing the analyte from the binding member, the method may include transferring the analyte away from the binding medium. For example, the method may include directing the released analyte downstream from the binding medium for secondary analysis with a secondary analysis device such as, but is not limited to, a UV spectrometer, and IR spectrometer, a mass spectrometer, an HPLC, an affinity assay device, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular weight, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes.

Figure 8:
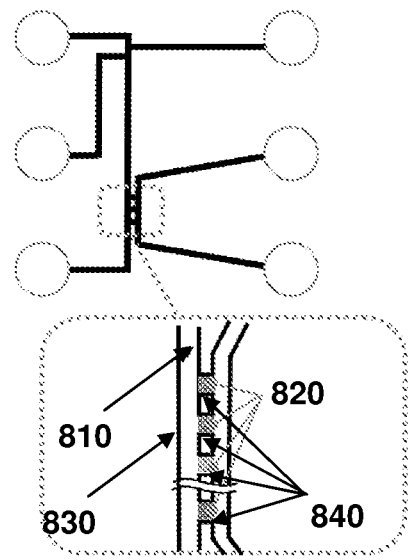
FIG. 8 shows a schematic of a microfluidic device configured for multiplex analysis of multiple analytes in a sample according to embodiments of the present disclosure.

FIG. 8 shows a schematic of a microfluidic device 800 configured for multiplex analysis of multiple analytes in a sample. The microfluidic device 800 includes a separation medium 810 in a separation channel 830, and multiple binding media 820 in corresponding individual binding channels 840. The separation medium 810 is in fluid communication with the multiple binding media 820. Each binding medium may include a different binding member. For example, each binding medium may include a different binding member that specifically binds a different analyte of interest. Analytes separated by the separation medium may be selectively transferred to the binding media 820. Detectable binding of an analyte to one of the binding media 820 indicates the presence of that particular analyte in the sample. Inclusion of multiple binding media 820, each bound to a different binding member, may facilitate the detection of multiple different analytes of interest in a single assay.

Figure 17:
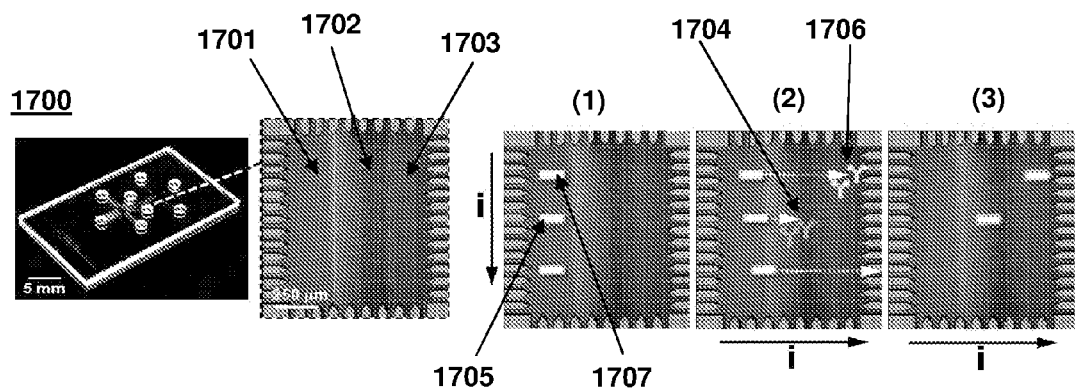
FIG. 17 shows images overlaid with schematics of the separation, transfer and detection of multiple analytes in a sample according to embodiments of the present disclosure.

FIG. 17 shows images overlaid with schematics of a microfluidic device 1700 configured for multiplex analysis of multiple analytes in a sample. The "i" indicates the direction of current flow for the separation step (1) and the transfer step (2). The microfluidic device 1700 includes a chamber containing a separation medium 1701, a first binding medium 1702 and a second binding medium 1703. The separation medium 1701 is in fluid communication with the first binding medium 1702, which is in fluid communication with the second binding medium 1703. Each binding medium may include a different binding member. For example, the first binding medium 1702 may include a first binding member 1704 that specifically binds a first analyte of interest 1705, and the second binding medium 1703 may include a second binding member 1706 that specifically binds a second analyte of interest 1707. Analytes in the sample are first separated by directing the sample through the separation medium (FIG. 17, step (1)). Analytes separated by the separation medium may be transferred to the first and second binding media 1702 and 1703, respectively (FIG. 17, step (2)). Detectable binding of the first analyte of interest 1705 to the first binding member 1704 in the first binding medium 1702 indicates the presence of the first analyte of interest 1705 in the sample (FIG. 17, step (3)). Detectable binding of the second analyte of interest 1707 to the second binding member 1706 in the second binding medium 1703 indicates the presence of the second analyte of interest 1707 in the sample (FIG. 17, step (3)). Inclusion of multiple binding media, each bound to a different binding member, may facilitate the detection of multiple different analytes of interest in a single assay.

In certain embodiments, the method is an automated method. As such, the method may include a minimum of user interaction with the microfluidic devices and systems after introducing the sample into the microfluidic device. For example, the steps of directing the sample through the separation medium to produce a separated sample and transferring the separated sample to the binding medium may be performed by the microfluidic device and system, such that the user need not manually perform these steps. In some cases, the automated method may facilitate a reduction in the total assay time. For example, embodiments of the method, including the separation and detection of analytes in a sample, may be performed in 30 min or less, such as 20 min or less, including 15 min or less, or 10 min or less, or 5 min or less, or 2 min or less, or 1 min or less.

FIG. 1A shows a schematic of a conventional immunoblotting procedure. First, the various analytes in a sample are separated by electrophoresis. Then the separated analytes are transferred to a membrane. Following blocking and washing, the analytes are probed with antibodies that specifically bind to certain target analytes.

FIG. 1B shows a schematic of an embodiment of a method for detecting the presence of an analyte in a sample. The method includes polyacrylamide gel electrophoresis (PAGE) followed by post-separation sample transfer and, finally, membrane-based affinity blotting. Analytes are electrokinetically transferred from a PAGE separation medium to a contiguous binding medium (e.g., a blotting gel) and are in-situ identified by specific affinity interactions. In step 1, the various analytes in a sample are separated by electrophoresis through a separation medium 5. The separation medium has a separation flow path with a first directional axis. An electric field is applied along the first directional axis to direct the sample through the separation medium 5. As the separated analytes reach the region in the separation medium 5 that is in fluid communication with the binding medium 4, specific analytes can be selectively transferred to the binding medium by applying an electric field along a second directional axis to direct the separated analyte to the binding medium (see FIG. 1B, step 2). The binding medium 4 includes binding members 7 bound to a support. For example, to form the binding medium 4, streptavidin acrylamide and biotinylated antibodies were copolymerized in polyacrylamide gels via projection lithography (330-375 nm, 4 min). In certain instances, the binding members are antibodies specific for a certain target analyte 6. If the target analyte 6 is present, the target analyte 6 will be retained in the binding medium 4 by binding to the binding member 7, producing a detectable signal (see FIG. 1B, step 3). If the target analyte is not present, no binding will occur to the binding member and thus, no detectable signal will be produced. If analytes other than the target analyte are present, they will not bind to the binding member and pass through the binding medium without binding to the binding member. Thus, no detectable signal will be produced.

Figure 7B:
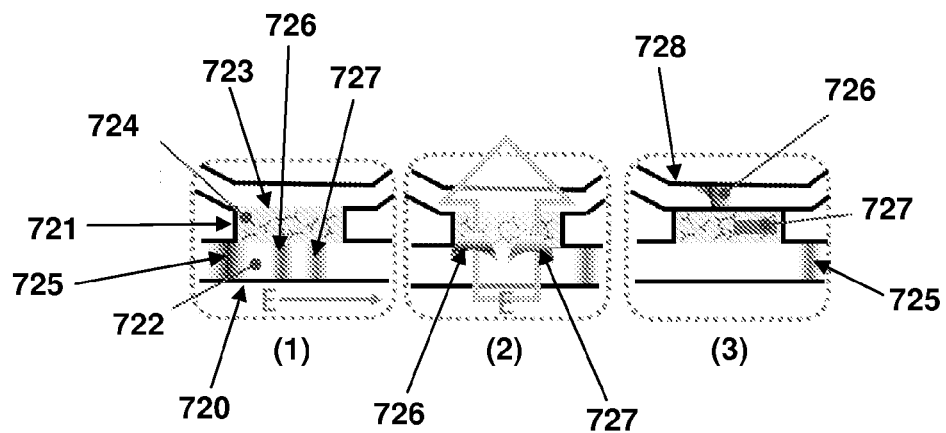
FIG. 7B shows a schematic of the separation, transfer and detection of an analyte in a sample according to embodiments of the present disclosure.

For embodiments of the microfluidic device 700 that include microfluidic channels in fluid communication with each other, FIG. 7B shows a schematic of the separation, transfer and detection of an analyte in a sample. Panel (1) in FIG. 7B shows the downstream end of the separation channel 720 that is in fluid communication with the binding channel 721. The separation channel 720 includes the separation medium 722 and the binding channel 721 includes the binding medium 723. The binding medium 723 includes binding members 724 bound to the binding medium 723. After electrophoretic separation (FIG. 7B, Panel (1)), analytes 725, 726 and 727 may be selectively electrophoretically transferred to and transported through the binding medium 723 (FIG. 7B, Panel (2)). Binding members 724 specifically bind to an analyte of interest 727, thus retaining the analyte of interest 727 in the binding medium 723 (FIG. 7B, Panel (3)). The analyte of interest 727 may include a detectable label, such as a fluorescent label, and thus the analyte of interest 727 bound to the binding medium 723 may be detected. Unbound analyte 726 is not specifically bound by the binding members 724 and passes through the binding medium 723 into the transfer channel 728, where the unbound analyte 726 may be directed to a waste reservoir or to downstream secondary analysis devices, as desired. Separated analytes 725 that are not transferred to the binding medium 723 remain in the separation channel 720 and may be directed to a waste reservoir or to downstream secondary analysis devices, as desired.

Systems

Aspects of certain embodiments include a system for detecting an analyte in a sample. In some instances, the system includes a microfluidic device as described herein. The system may also include a detector. In some cases, the detector is a detector configured to detect a detectable label. As described above, the detectable label may be a fluorescent label. For example, the fluorescent label can be contacted with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected with an appropriate detector to determine the presence of the analyte bound to the binding member.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, sample solutions, buffers (e.g., release buffers, wash buffers, electrophoresis buffers, etc.), and the like. In certain embodiments, the microfluidic fluid handling components are configured to deliver a fluid to the separation medium of the microfluidic device, such that the fluid contacts the separation medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 μL or less, including 100 μL or less, for example 50 μL or less, or 25 μL or less, or 10 μL or less, or 5 μL or less, or 1 μL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium. In some cases, the applied electric field may be aligned with the directional axis of the separation flow path of the separation medium. As such, the applied electric field may be configured to electrokinetically transport the analytes and moieties in a sample through the separation medium. In certain embodiments, the system includes an electric field generator configured to apply an electric field such that analytes and/or moieties in the sample are electrokinetically transported from the separation medium to the binding medium. For instance, an applied electric field may be aligned with the directional axis of the labeling flow path of the binding medium. In some cases, the applied electric field is configured to electrokinetically transport selected analytes that have been separated by the separation medium. Selected analytes that have been separated by the separation medium may be transported to the binding medium by applying an appropriate electric field along the directional axis of the labeling flow path of the binding medium. In some instances, the electric field generators are configured to apply an electric field with a strength ranging from 10 V/cm to 1000 V/cm, such as from 100 V/cm to 800 V/cm, including from 200 V/cm to 600 V/cm.

In certain embodiments, the electric field generators include voltage shaping components. In some cases, the voltage shaping components are configured to control the strength of the applied electric field, such that the applied electric field strength is substantially uniform across the separation medium and/or the binding medium. The voltage shaping components may facilitate an increase in the resolution of the analytes in the sample. For instance, the voltage shaping components may facilitate a reduction in non-uniform movement of the sample through the separation medium. In addition, the voltage shaping components may facilitate a minimization in the dispersion of the bands of analytes as the analytes traverses the separation medium.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, 8 or more, 10 or more, 50 or more, or 100 or more microfluidic devices. In certain embodiments, the microfluidic devices can be arranged into an array with an area of less than 10 cm$^2$, or less than 5 cm$^2$, e.g., less than 1 cm$^2$, including less than 50 mm$^2$, less than 20 mm$^2$, such as less than 10 mm$^2$, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 µL or less, such as 75 µL or less, including 50 µL or less, or 25 µL or less, or 10 µL or less, for example, 5 µL or less, 2 µL or less, or 1 µL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 µg/mL or less, such as 500 ng/mL or less, including 100 ng/mL or less, for example, 10 mg/mL or less, or 5 ng/mL or less, such as 1 ng/mL or less, or 0.1 ng/mL or less, or 0.01 ng/mL or less, including 1 µg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

Utility

The subject devices, systems and methods find use in a variety of different applications where determination of the presence or absence, and/or quantification of one or more analytes in a sample is desired. In certain embodiments, the methods are directed to the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, in the ongoing management or treatment of a disease condition in a subject, etc. In addition, the subject devices, systems and methods may find use in protocols for the detection of an analyte in a sample, such as, but not limited to, Western blotting, Southern blotting, Northern blotting, Eastern, Far-Western blotting, Southwestern blotting, and the like.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods finds use in portable and point-of-care or near-patient molecular diagnostics.

In certain embodiments, the subject devices, systems and methods find use in detecting biomarkers for a disease or disease state. In some cases, the disease is a cellular proliferative disease, such as but not limited to, a cancer, a tumor, a papilloma, a sarcoma, or a carcinoma, and the like. In certain instances, the subject devices, systems and methods find use in detecting biomarkers for the characterization of cell signaling pathways and intracellular communication for drug discovery and vaccine development. For example, the subject devices, systems and methods find use in detecting the presence of a disease, such as a cellular proliferative disease, such as a cancer, tumor, papilloma, sarcoma, carcinoma, or the like. In certain instances, particular biomarkers of interest for detecting cancer or indicators of a cellular proliferative disease include, but are not limited to the following: prostate specific antigen (PSA), which is a prostate cancer biomarker; C-reactive protein, which is an indicator of inflammation; transcription factors, such as p53, which facilitates cell cycle and apoptosis control; polyamine concentration, which is an indicator of actinic keratosis and squamous cell carcinoma; proliferating cell nuclear antigen (PCNA), which is a cell cycle related protein expressed in the nucleus of cells that are in the proliferative growth phase; growth factors, such as IGF-I; growth factor binding proteins, such as IGFBP-3; micro-RNAs, which are single-stranded RNA molecules of about 21-23 nucleotides in length that regulate gene expression; carbohydrate antigen CA19.9, which is a pancreatic and colon cancer biomarker; cyclin-dependent kinases; epithelial growth factor (EGF); vascular endothelial growth factor (VEGF); protein tyrosine kinases; over-expression of estrogen receptor (ER) and progesterone receptor (PR); and the like. For example, the subject devices, systems and methods may be used to detect and/or quantify the amount of endogenous prostate specific antigen (PSA) in diseased, healthy and benign samples.

In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like. For example, the subject devices, systems and methods may be used to monitor HIV viral load and patient CD4 count for HIV/AIDS diagnosis and/or therapy monitoring by functionalizing the sensor surface with antibodies to HIV capsid protein p24, glycoprotiens 120 and 41, CD4+ cells, and the like. Particular diseases or disease states that may be detected by the subject devices, systems and methods include, but are not limited to, bacterial infections, viral infections, increased or decreased gene expression, chromosomal abnormalities (e.g. deletions or insertions), and the like. For example, the subject devices, systems and methods can be used to detect gastrointestinal infections, such as but not limited to, aseptic meningitis, botulism, cholera, *E. coli* infection, hand-foot-mouth disease, *helicobacter* infection, hemorrhagic conjunctivitis, herpangina, myocaditis, paratyphoid fever, polio, shigellosis, typhoid fever, vibrio septicemia, viral diarrhea, etc. In addition, the subject devices, systems and methods can be used to detect respiratory infections, such as but not limited to, adenovirus infection, atypical pneumonia, avian influenza, swine influenza, bubonic plague, diphtheria, influenza, measles, meningococcal meningitis, mumps, parainfluenza, pertussis (i.e., whooping chough), pneumonia, pneumonic plague, respiratory syncytial virus infection, rubella, scarlet fever, septicemic plague, severe acute respiratory syndrome (SARS), tuberculosis, etc. In addition, the subject devices, systems and methods can be used to detect neurological diseases, such as but not limited to, Creutzfeldt-Jakob disease, bovine spongiform encephalopathy (i.e., mad cow disease), Parkinson's disease, Alzheimer's disease, rabies, etc. In addition, the subject devices, systems and methods can be used to detect urogenital diseases, such as but not limited to, AIDS, chancroid, Chlamydia, condyloma accuminata, genital herpes, gonorrhea, lymphogranuloma venereum, non-gonococcal urethritis, syphilis, etc. In addition, the subject devices, systems and methods can be used to detect viral hepatitis diseases, such as but not limited to, hepatitis A, hepatitis B, hepatitis C, hepatitis D, hepatitis E, etc. In addition, the subject devices, systems and methods can be used to detect hemorrhagic fever diseases, such as but not limited to, Ebola hemorrhagic fever, hemorrhagic fever with renal syndrome (HFRS), Lassa hemorrhagic fever, Marburg hemorrhagic fever, etc. In addition, the subject devices, systems and methods can be used to detect zoonosis diseases, such as but not limited to, anthrax, avian influenza, brucellosis, Creutzfeldt-Jakob disease, bovine spongiform encephalopathy (i.e., mad cow disease), enterovirulent *E. coli* infection, Japanese encephalitis, leptospirosis, Q fever, rabies, sever acute respiratory syndrome (SARS), etc. In addition, the subject devices, systems and methods can be used to detect arbovirus infections, such as but not limited to, Dengue hemorrhagic fever, Japanese encephalitis, tick-borne encephalitis, West Nile fever, Yellow fever, etc. In addition, the subject devices, systems and methods can be used to detect antibiotics-resistance infections, such as but not limited to, *Acinetobacter baumannii, Candida albicans, Enterococci* sp., *Klebsiella pneumoniae, Pseudomonas aeruginosa, Staphylococcus aureus*, etc. In addition, the subject devices, systems and methods can be used to detect vector-borne infections, such as but not limited to, cat scratch disease, endemic typhus, epidemic typhus, human ehrlichosis, Japanese spotted fever, louse-borne relapsing fever, Lyme disease, malaria, trench fever, Tsutsugamushi disease, etc. Similarly, the subject devices, systems and methods can be used to detect cardiovascular diseases, central nervous diseases, kidney failures, diabetes, autoimmune diseases, and many other diseases.

The subject device, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described in detail herein. The kits may further include a buffer. For instance, the kit may include a buffer, such as an electrophoretic buffer, a sample buffer, and the like. The kits may further include additional reagents, such as but not limited to, release agents, denaturing agents, refolding agents, detergents, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Materials and Methods

Unless otherwise stated below, microfluidic devices were prepared and experiments were performed using the following protocol.

Reagents

The water-soluble photoinitiator 2,2-azobis[2-methyl-N-(2-hydroxyethyl) propionamide] (VA-086) was purchased from Wako Chemicals (Richmond, Va.). 3-(trimethoxysilyl)-propyl methacrylate (98%), glacial acetic acid (ACS grade), methanol (ACS grade) and 30% (29:1) acrylamide/bis-acrylamide were purchased from Sigma (St. Louis, Mo.). Streptavidin-acrylamide (SA) was purchased from Invitrogen (Carlsbad, Calif.). Premixed 10× Tris-glycine native electrophoresis buffer (25 mM Tris, pH 8.3, 192 mM glycine) was purchased from Bio-Rad (Hercules, Calif.). Alexa Fluor 488 conjugated bovine serum albumin (BSA) and FITC-biotin were used as negative and positive controls, respectively (Sigma Aldrich, St. Louis, Mo.). α-actinin and biotin conjugated anti-actinin were purchased from Cytoskeleton, Inc. (Denver, Colo.). Free PSA (Prostate Specific Antigen) and biotinylated monoclonal anti-PSA were purchased from EXBIO (Praha, Czech Republic). The proteins were fluorescently labeled in-house using Alexa Fluor 488 protein labeling kits per the supplier's instructions (Invitrogen, Carlsbad, Calif.). Labeled proteins were stored at 4° C. in the dark until use.

Microfluidic Chip Fabrication

Glass microfluidic chips were designed in-house and fabricated using standard wet etch processes by Caliper Life Sciences (Hopkinton, Mass.). Surfaces were first functionalized for covalent linkage to polyacrylamide (PA) gel using a 2:3:2:3 ratio mixture of 3-(trimethoxysilyl) propyl methacrylate, glacial acetic acid, deionized water, and methanol. After a 20-min static incubation, methanol was flushed through the microfluidic device for 30 min followed by a drying nitrogen purge.

Functionalized Binding Medium Photopatterning

Mask-based lithography via a UV objective (UPLANS-APO 4×, Olympus) in combination with a film mask and microscope system (IX-70, Olympus, Melville, N.Y.) provided excitation resulting in cross-linking and formation of the binding medium (8% T, including streptavidin-acrylamide). Covalently bonded streptavidin in gel matrix was used to immobilize biotinylated antibodies for immunoblotting. A mercury bulb was used as the excitation source (330-375 nm) and mask alignment to the chip was performed using a manual adjust x-y translation stage on the microscope (Olympus, Melville, N.Y.). The final precursor volume, including the acrylamide and BIS, was adjusted with Tris-glycine native running buffer containing 0.2% (w/v) VA-086 photoinitiator. The gel precursor solutions were degassed (5 min under vacuum while sonicated with agitation) just prior to loading into the microfluidic device to ensure a final gel that was substantially bubble-free. To initiate fabrication, PA gel precursor solutions were wicked or gently pressure-filled (via syringe) into the microfluidic device. After the microfluidic device was loaded, a high viscosity 5% 2-hydroxyethyl cellulose solution (Sigma, average MW~720,000) was gently introduced by pipette onto each reservoir. A larger pore-size sample loading gel was formed using flood exposure of the chip to a filtered mercury lamp (300-380 nm) located 15 cm away (100 W, UVP B100-AP, Upland, Calif.) with cooling fan.

Apparatus and Imaging

Assay operation was programmable and controlled via a high voltage power supply equipped with platinum electrodes (Labsmith HVS448, Livermore, Calif.). Samples were loaded by applying a +800 V potential at the sample waste reservoir and grounding the sample reservoir for ~2 min. Images were collected using an inverted epi-fluorescence microscope (IX-70, Olympus, Melville, N.Y.) equipped with a 10× objective (N.A. 0.3), filter cube optimized for GFP detection and an x-y translation stage. A 1392×1040 Peltier-cooled interline CCD camera (CoolSNAP™ HQ2, Roper Scientific, Trenton N.J.) was used to monitor protein migration and binding with a 10 MHz frequency. Unless otherwise stated, the CCD exposure time was 300 ms. Image analysis was completed using ImageJ (National Institutes of Health, Bethesda, Md.).

Results

Figure 2:
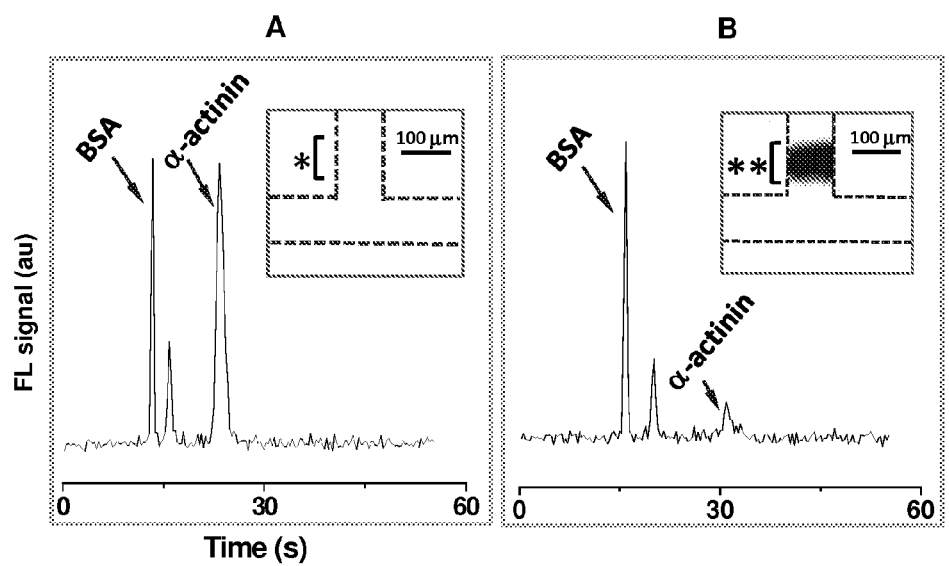
FIG. 2 shows electropherograms of proteins before (FIG. 2A) and after (FIG. 2B) transferring the separated sample to the binding medium according to embodiments of the present disclosure.

FIG. 2 shows electropherograms of proteins before (FIG. 2A) and after (FIG. 2B) transferring the separated sample to the binding medium. Native PAGE of target proteins (α-actinin and prostate specific antigen, PSA) and negative control (BSA), with subsequent electrophoretic transfer to the binding medium was performed. Separated protein bands were transferred to the binding medium in 30 seconds or less with 85% capture efficiency. The specific target protein (slowest peak, α-actinin) bound to the binding medium and yielded a detectable fluorescence signal (FIG. 2B, inset, inverted grayscale).

Figure 3:
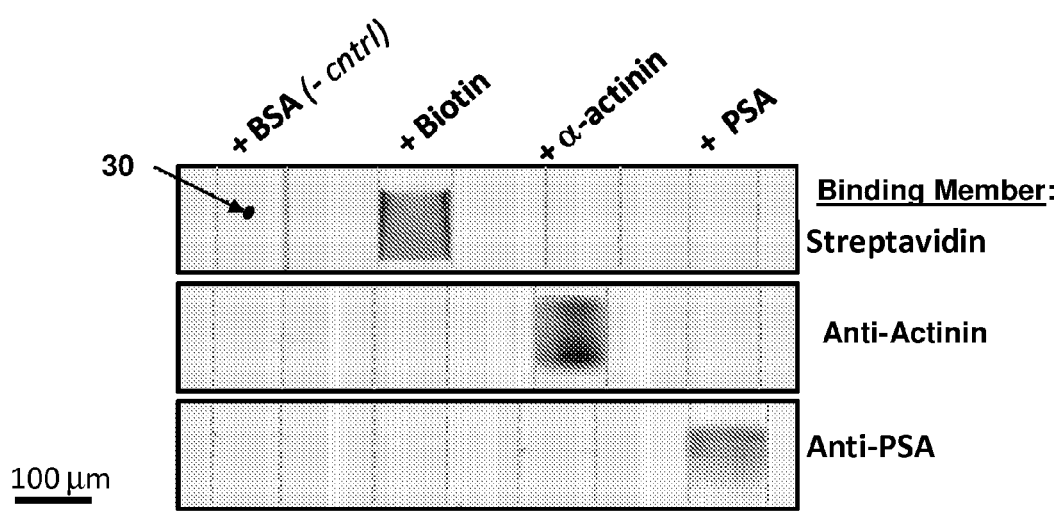
FIG. 3 shows fluorescence images of experiments testing assay specificity using positive and negative protein controls according to embodiments of the present disclosure. Images show fluorescence of proteins bound to in-channel antibody-functionalized membranes.

FIG. 3 shows fluorescence images of experiments testing assay specificity using positive and negative protein controls. Fluorescence images of the binding medium 30 of microfluidic devices are shown in FIG. 3. Analytes BSA (e.g., a negative control), biotin, α-actinin and PSA were individually contacted to three different binding media with streptavidin, anti-actinin, and anti-PSA bound to the binding medium support, respectively. FIG. 3 shows no detectable off-diagonal signal, indicating no detectable cross-reactivity and no detectable non-specific adsorption.

Figure 4:
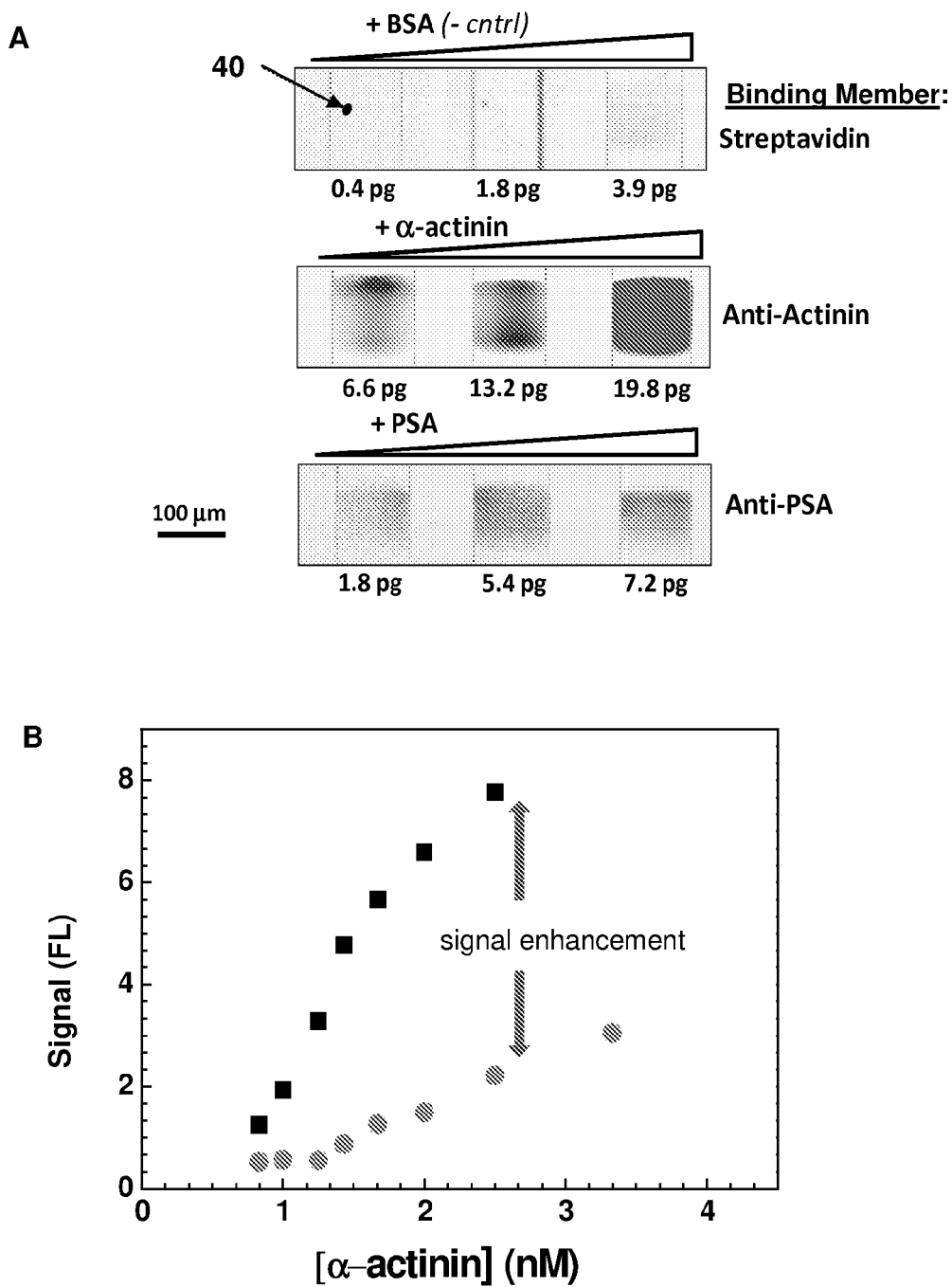
FIG. 4A shows fluorescence images of the dose response of proteins bound to antibody-functionalized binding media in a microfluidic device according to embodiments of the present disclosure.
FIG. 4B shows a graph of fluorescence signal vs. protein concentration for an analyte bound to a binding medium according to embodiments of the present disclosure.

FIG. 4A shows fluorescence images of the dose response of proteins bound to antibody-functionalized binding media in a microfluidic device. Fluorescence images of the binding medium 40 of microfluidic devices are shown in FIG. 4. Increasing concentrations of BSA (e.g., a negative control) were contacted to a binding medium functionalized with streptavidin. BSA showed no or minimal detectable signal. Increasing concentrations of α-actinin were contacted to a binding medium functionalized with anti-actinin. α-actinin showed an increase in fluorescence signal as the concentration of α-actinin increased. Increasing concentrations of PSA were contacted to a binding medium functionalized with anti-PSA. PSA showed an increase in fluorescence signal as the concentration of PSA increased. Establishment of dose-response curves may facilitate protein quantitation. In addition, intrinsic protein enrichment on the binding medium was observed (see FIG. 4B). The protein enrichment may facilitate an increase in detection sensitivity on the binding medium, as compared to the signal in the absence of the binding medium.

Figure 5:
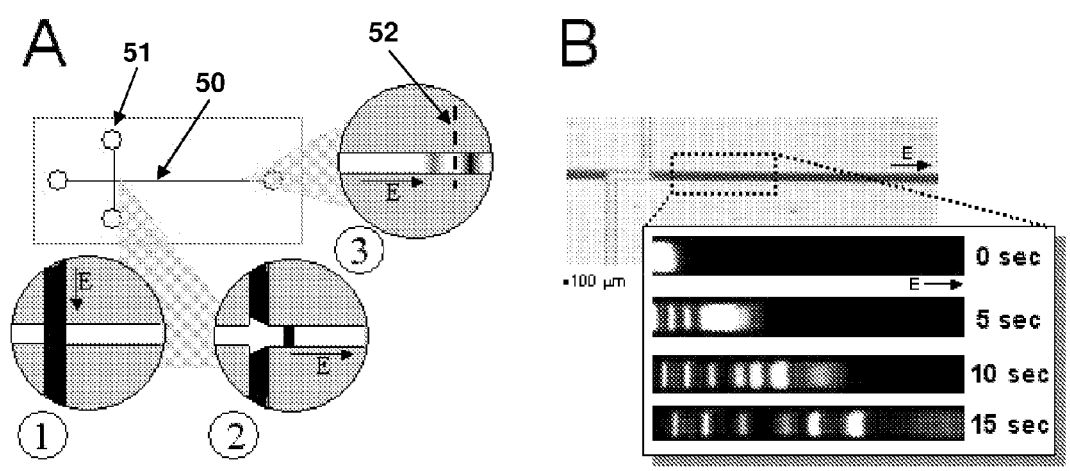
FIG. 5A shows a schematic of a microfluidic device that includes a separation medium according to embodiments of the present disclosure.
FIG. 5B shows a high-resolution electrophoretic analysis of a wide molecular range protein ladder using a microfluidic device according to embodiments of the present disclosure.

FIG. 5A shows a schematic of a microfluidic device that includes a separation medium 50. A sample can be introduced into the microfluidic device through sample inlet 51. The sample can be loaded onto the separation medium 50 by applying an electric field to direct the sample from the sample inlet 51 to the separation medium 50 (see FIG. 5A, inset 1). After the sample is contacted with the separation medium 50 an electric field can be applied along the directional axis of the separation medium 50 to direct the sample through the separation medium 50 (see FIG. 5A, inset 2). The analytes in the sample can be separated as they flow through the separation medium 50 and detected by detector 52 positioned at the distal end of the separation medium 50. FIG. 5B shows a high-resolution electrophoretic analysis of a wide molecular range protein ladder using a microfluidic device with a separation medium prepared by photopatterning a cross-linked polyacrylamide gel. The separation medium was able to achieve detectable resolution between the different proteins in the sample after 15 seconds using a sample volume of $10 \times 10^{-6}$ L.

Figure 6:
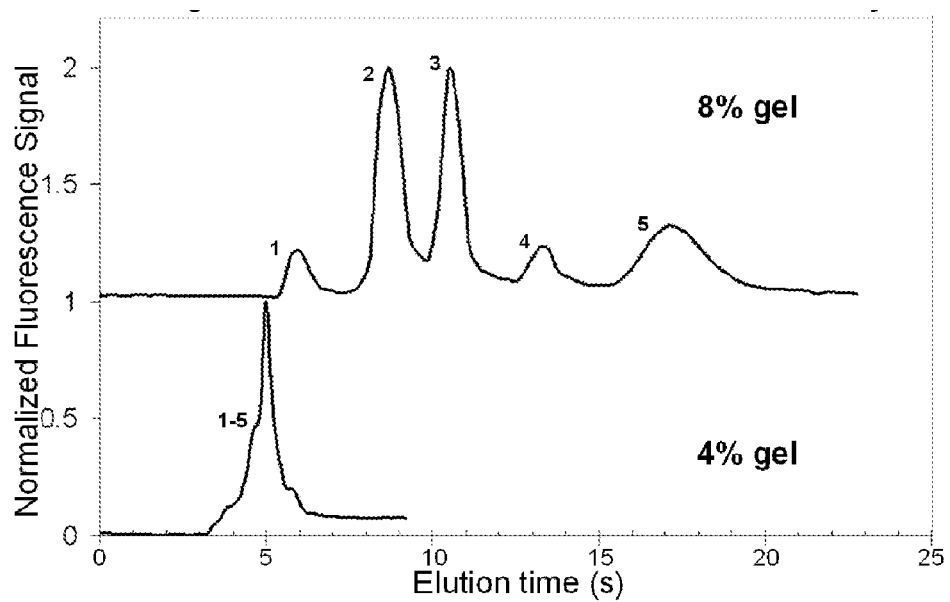
FIG. 6 shows electropherograms of five low-molecular weight proteins for a 8% total acrylamide gel (top graph) and a 4% total acrylamide gel (bottom graph) according to embodiments of the present disclosure.

FIG. 6 shows an example of the difference in resolution of polyacrylamide gels in the electrophoretic separation of five low-molecular weight proteins. In FIG. 6 a polyacrylamide gel with 8% total acrylamide (e.g., a small pore size gel) was able to detectably resolve all five proteins in the sample in 20 seconds (see FIG. 6, top graph), whereas a polyacrylamide gel with 4% total acrylamide (e.g., a large pore size gel) was not able to resolve the proteins in the sample and only gave a single peak at 5 seconds (see FIG. 6, bottom graph).

Figure 9A:
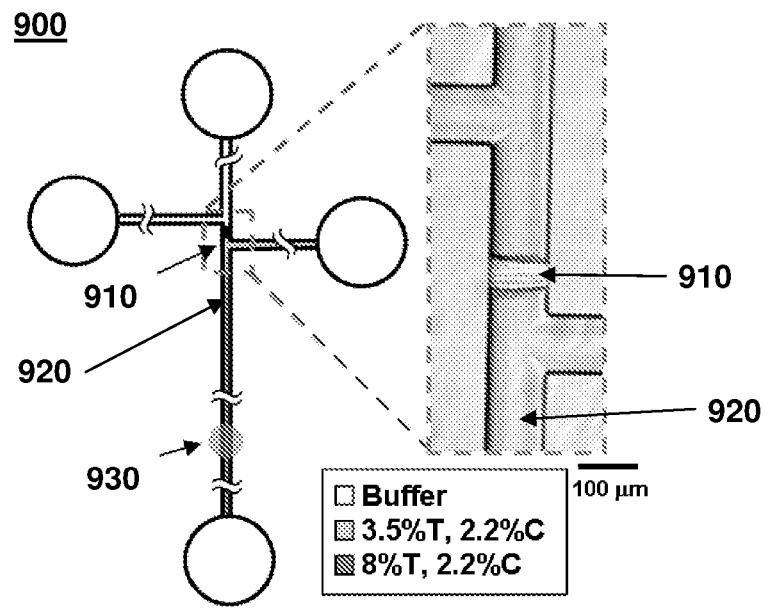
FIG. 9A shows a schematic and image (inset) of a microfluidic device that includes a concentration medium upstream from a separation medium according to embodiments of the present disclosure.
Figure 9B:
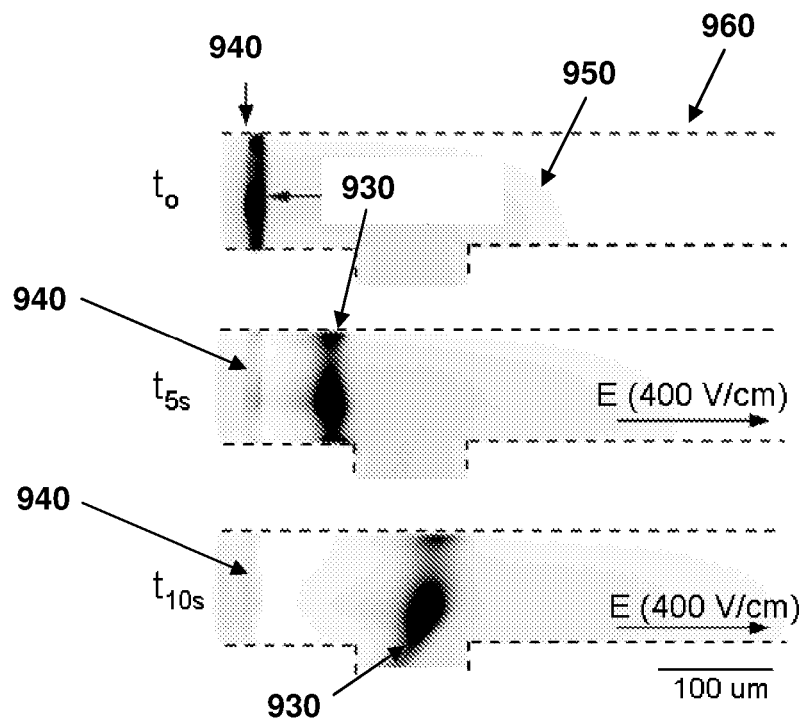
FIG. 9B shows images of the electrophoretic movement of a sample through a microfluidic device that includes a concentration medium upstream from a separation medium according to embodiments of the present disclosure.

FIG. 9A shows a schematic and image (inset) of a microfluidic device 900 that included a concentration medium 910 upstream from a separation medium 920. The upstream region of the separation medium 920 included a large pore size gel with 3.5% total acrylamide (T) and 2.2% cross-linker (C). Downstream from the large pore size region of the separation medium was a small pore size region with 8% T and 2.2% C. FIG. 9B shows images of the electrophoretic movement over time of a sample 930 through a microfluidic device that included a concentration medium 940 upstream from a separation medium 950. The separation medium included a 6% polyacrylamide gel in a separation channel 960. Inverted fluorescence micrographs were taken at 5 second time intervals, $t_0$, $t_5$, and $t_{10}$. The fluorescence micrographs show sample enrichment and elution of the protein sample near the concentration medium 940. In FIG. 9B, concentrated reporter protein (e.g., fluorescently labeled anti-C-RP) at an initial concentration of 100 nM was enriched 170 times at the concentration medium (e.g. a membrane) after 3 min. Enriched anti-C-RP eluted into separation channel in 10 s. The applied electric field was 400 V/cm.

Figure 10:
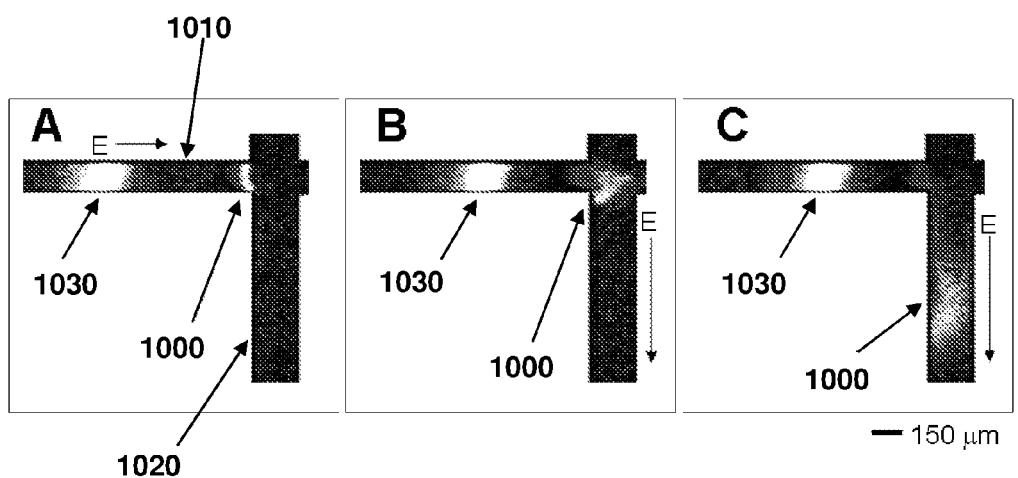
FIG. 10 shows images of selective transfer of an analyte of interest from a first microfluidic channel to a second microfluidic channel according to embodiments of the present disclosure.

FIG. 10 shows images of selective transfer of an analyte of interest 1000 after electrophoretic analysis from a first microfluidic channel 1010 to a second microfluidic channel 1020. Selective transfer of specific analytes of interest enables protein collection for contacting with a binding medium or for subsequent analysis. In FIG. 10, an analyte of interest 1000 was directed from an electrophoretic separation in the first microfluidic channel 1010 to a second microfluidic channel 1020 for further analysis. Analytes not of interest 1030 remained undisturbed in the first microfluidic channel 1010. Selective transfer of an analyte of interest from one microfluidic channel to another may facilitate quantitative manipulation of small volumes (e.g., less than 1 µL). In addition, physical manipulation of specific resolved analytes may facilitate post-electrophoretic characterization of selected analytes of interest. In FIG. 10, proteins were electrophoretically separated (e.g., isoelectric focusing) in the first microfluidic channel 1010. To transfer an analyte of interest 1000 located at the intersection between the first microfluidic channel 1010 and the second microfluidic channel 1020, an electric field was applied across the intersection (E=395 V/cm), perpendicular to the initial electric field used for the separation of the analytes, to drive the analyte of interest 1000 into the second microfluidic channel 1020.

Figure 11:
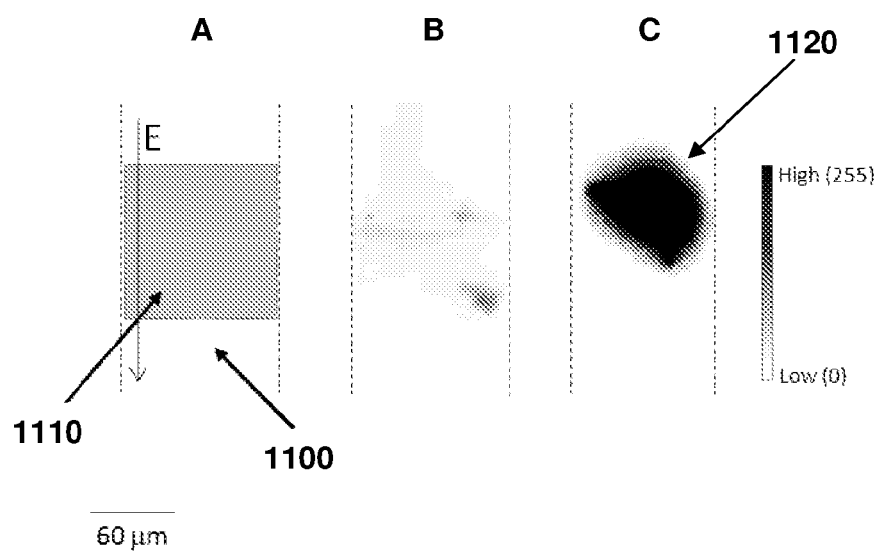
FIG. 11 shows a schematic of a binding medium and images of a binding medium exposed to negative and positive controls according to embodiments of the present disclosure.
Figure 12:
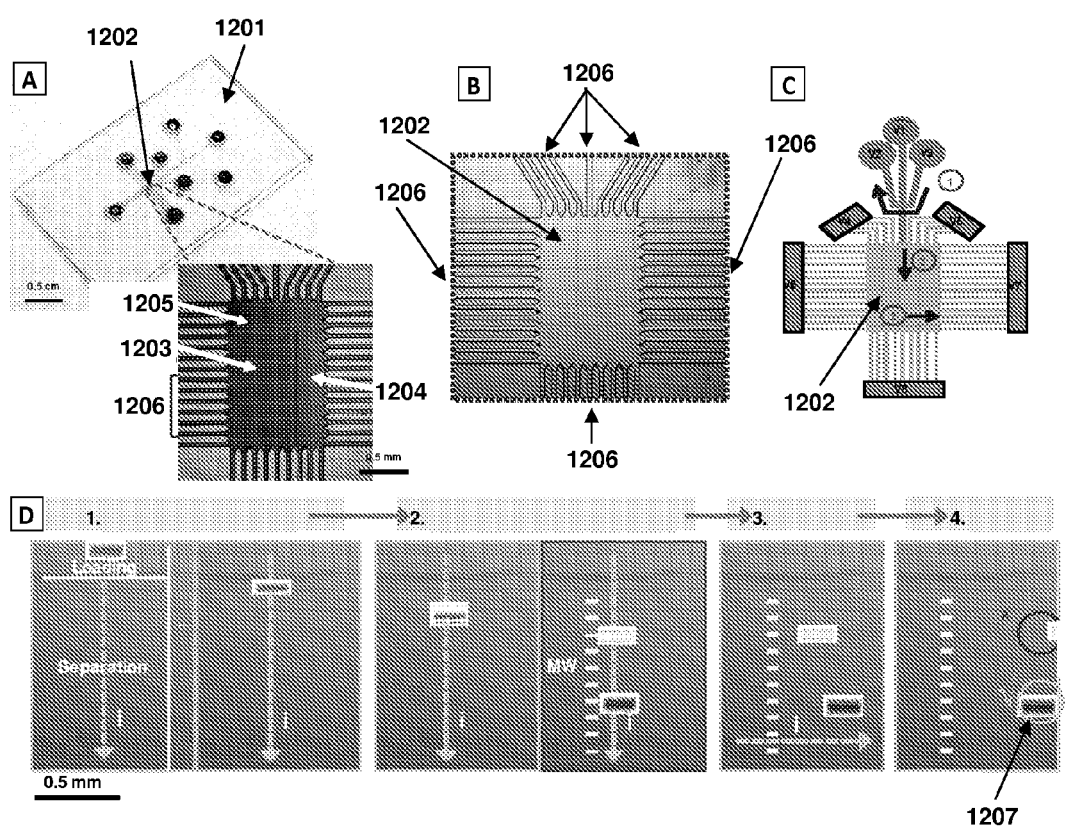
FIG. 12A shows bright field images of a microfluidic device that includes a chamber (inset) containing a loading medium, a separation medium and a binding medium according to embodiments of the present disclosure.
FIG. 12B shows an image of the chamber according to embodiments of the present disclosure.
FIG. 12C shows a schematic of a microfluidic device that includes a chamber according to embodiments of the present disclosure.
FIG. 12D shows images overlaid with schematics of the separation, transfer and detection of an analyte in a sample according to embodiments of the present disclosure.

FIG. 11A shows a schematic of a binding medium 1110 positioned in a microfluidic channel 1100. In addition, electric field (E) is indicated showing the direction of electrophoresis through the binding medium. FIGS. 11B and 11C show fluorescence images of a binding medium exposed to negative and positive controls. 200 nM IgG was copolymerized in a polyacrylamide binding medium (10% total acrylamide/2.5% cross-linker). The binding medium was formed by a 20 second exposure to a thin (75 µm wide) laser sheet from a 100 W 365-nm YAG laser in a glass microchannel. 1:100 IgG-FITC and 1:100 Protein G-FITC solutions were electrophoresed through the binding medium at 600 V for 5-min, followed by a buffer for 15-min to flush unbound Protein G*. Fluorescence imaging was performed by CCD/ epi-fluorescence microscopy. The fluorescence images shown in FIGS. 11B and 11C illustrate the specific interaction of copolymerized antibody to Protein G (IgG) with fluorescently labeled Protein G (Protein G*). FIG. 11B was a negative control (e.g., no copolymerized IgG in the binding medium) and showed negligible detectable signal from fluorescently labeled Protein G that had been electrophoresed. In FIG. 11C, the binding medium copolymerized with IgG bound Protein G*. The results indicated that the specificity of the antibodies bound to the binding medium was retained during electrophoretic analyte transport.

FIG. 12A shows bright field images of a microfluidic device 1201 that included a chamber (inset) 1202 containing a separation medium 1203 and a binding medium 1204. The binding medium 1204 was disposed in fluid communication with the separation medium 1203 and aligned along the labeling flow path (see FIG. 12C, step 3). In this case, the separation flow path (see FIG. 12C, step 2) and the labeling flow path (see FIG. 12C, step 3) were orthogonal to each other. The labeling medium included a gel that was similar in pore-size to the separation medium. In addition, the labeling medium included streptavidin to allow functionalization with biotinylated binding members (e.g., antibodies). The chamber 1202 also included a loading medium 1205 in fluid communication with the separation medium 1203. The loading medium 1205 was disposed upstream from the separation medium 1203 along the separation flow path (see FIG. 12C, step 2). The loading medium 1205 included a large pore-size gel (3% total acrylamide) upstream from a smaller pore-size separation medium 1203 (6% total acrylamide). The chamber 1202 in FIG. 12A is also in fluid communication with a plurality of channels 1206 disposed along the sides of the chamber 1202. The channels 1206 may be configured to direct an electric field to the loading medium 1205, separation medium 1203 and binding medium 1204 in the chamber 1202.

FIG. 12B shows a bright field image of the chamber 1202 and channels 1206 configured to direct an electric field to the chamber 1202. FIG. 12C shows a schematic of a microfluidic device that includes a chamber 1202 as described above. Sample may be introduced into the microfluidic device (see FIG. 12C, step 1). An electric field may be applied along the directional axis of the separation flow path to direct the sample through the loading medium and the separation medium (see FIG. 12C, step 2). The electric fields may be applied using electric field generators, V1, V2, V3, V4, V5, V6, V7 and V8. After electrophoretic separation of the sample, the separated analytes in the sample may be selectively transferred to the binding medium by applying an electric field along the directional axis of the labeling flow path (see FIG. 12C, step 3).

FIG. 12D shows images overlayed with schematics of the separation, transfer and detection of an analyte in a sample. Protein sample was first electrokinetically loaded into the large pore-size loading medium of the microfluidic device (see FIG. 12D, step 1). The protein sample was concentrated upon reaching the interface between the large pore-size loading medium and the smaller pore-size separation medium. "i" indicates the direction of electrical current flow. Proteins were separated as they migrated along the directional axis of the separation flow path towards the bottom of the separation medium (see FIG. 12D, step 2). The applied electric field was then switched to direct the separated proteins into the binding medium, which included immobilized (e.g., cross-linked or copolymerized) binding members (see FIG. 12D, step 3). The binding members were configured to specifically bind to and retain the analyte of interest 1207 and yielded a positive "blot" (e.g., a detectable signal) if the analyte of interest 1207 bound to the functionalized binding medium. Molecular weight and binding information was determined to identify the analyte of interest 1207.

Figure 13:
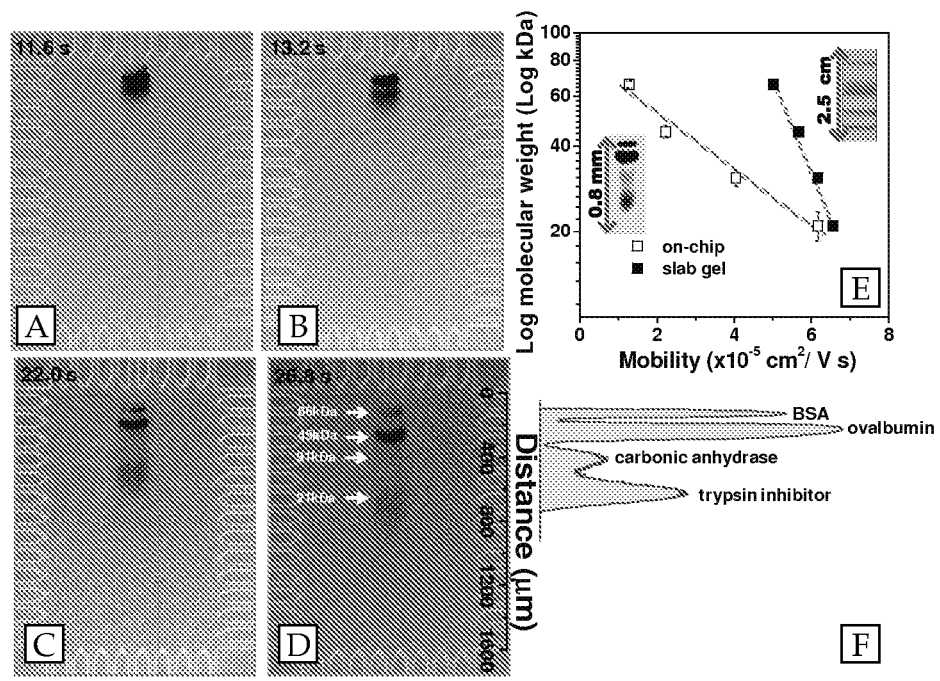
FIG. 13 shows images and graphs of the separation of a protein ladder in a microfluidic device according to embodiments of the present disclosure.

FIG. 13 shows images and graphs of the separation of a protein ladder in a microfluidic device. FIGS. 13A-13D show inverted CCD images of an electrophoretic separation of a protein ladder using 12% SDS-PAGE in a microfluidic device. The images in FIGS. 13A-13D were captured at various time points (e.g., 11.6 sec, 13.2 sec, 22.0 sec and 26.8 sec after the start of the electrophoretic separation). In FIG. 13E, the migration mobility of the protein ladder was linearly related to the size of the protein by a microfluidic device using SDS-PAGE (3%-8% T). Results were compared to a gradient slab gel (4%-12% T) SDS-PAGE (see FIG. 13E). The inserts in the graph in FIG. 13E show the protein bands separated by the microfluidic device and the slab gel. FIG. 13F shows an electropherogram of the SDS-PAGE separation using the microfluidic device. The migration distance was scaled to the CCD image in FIG. 13D.

Figure 14A:
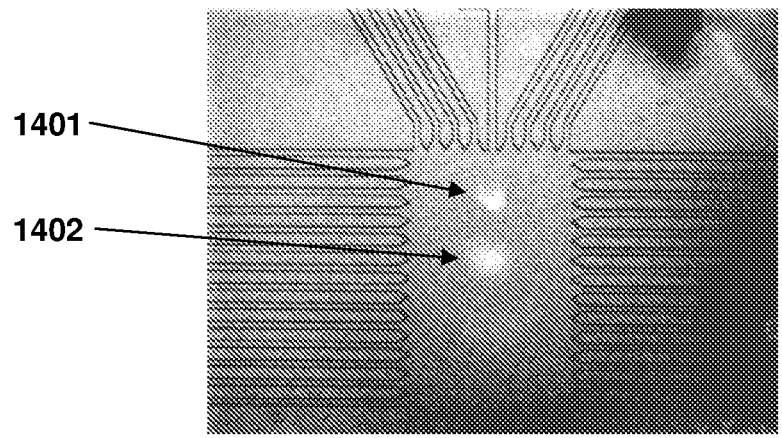
FIG. 14A shows an image of the separation of fluorescently labeled proteins using a microfluidic device according to embodiments of the present disclosure.
Figure 14B:
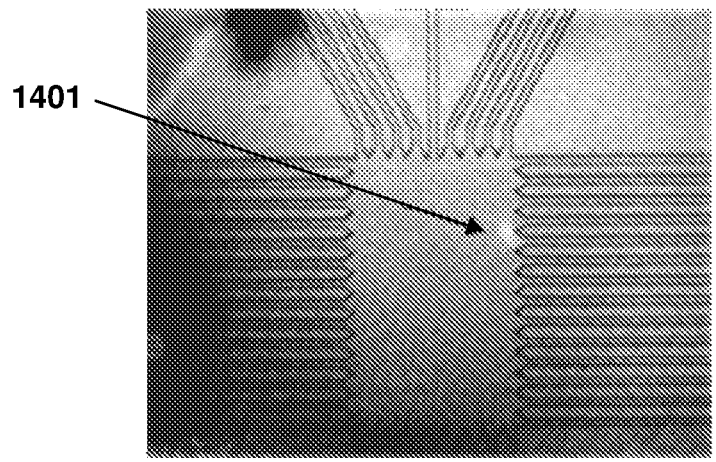
FIG. 14B shows an image of the transfer of a fluorescently labeled protein from the separation medium to the binding medium in a microfluidic device according to embodiments of the present disclosure.
Figure 15:
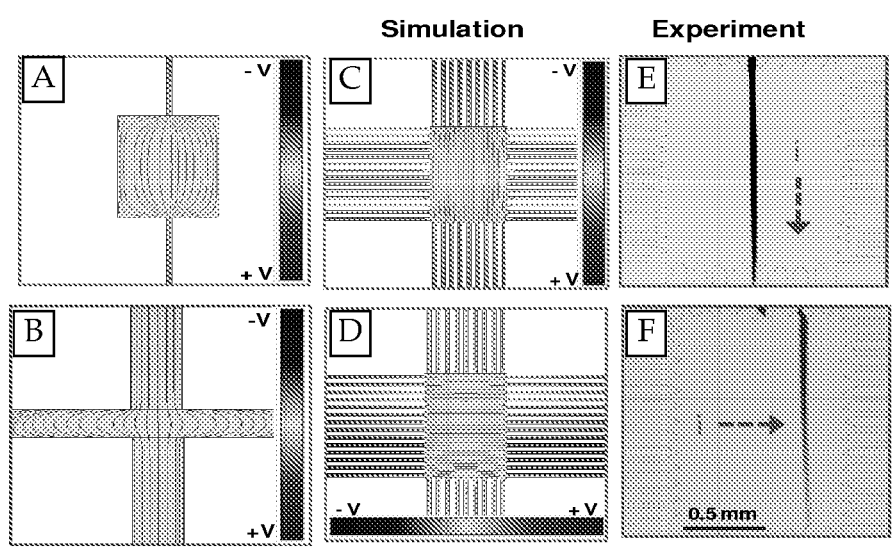
FIGS. 15A-15D show images of simulated electric field distributions for microfluidic devices according to embodiments of the present disclosure.
FIGS. 15E-15F shows images of a microfluidic device testing the uniformity of the applied electric field according to embodiments of the present disclosure.

FIG. 14A shows an image of the separation of fluorescently labeled proteins using a microfluidic device. Fluorescently labeled, biotinylated actin 1401 was separated from other proteins in a sample using SDS-PAGE in the microfluidic device. The larger protein species (e.g., the fluorescently labeled, biotinylated actin 1401) migrated a shorter distance through the separation medium than the smaller protein species 1402. FIG. 14B shows an image of the transfer of a fluorescently labeled protein from the separation medium to the binding medium in the microfluidic device. The binding medium included streptavidin bound to the binding medium. The binding medium specifically bound to and retained the fluorescently labeled, biotinylated actin 1401 as the fluorescently labeled, biotinylated actin 1401 traversed the binding medium (see FIG. 14B). The smaller protein species 1402 traversed the binding medium without binding to the binding medium and exited the microfluidic device.

FIGS. 15A-15D show images of simulated electric field distributions for microfluidic devices. FIGS. 15A and 15B show images for COMSOL simulated 1-dimensional electric field distributions in a microfluidic chamber and a microfluidic device with a main channel and one cross-channel, respectively. FIGS. 15C and 15D, respectively, show images for the vertical and horizontal COMSOL simulated 2-dimensional electric field distributions in a microfluidic chamber. The COMSOL simulation indicated that the vertical and horizontal electric field distributions in the microfluidic chamber were uniform across the microfluidic chamber. FIGS. 15E-15F show CCD images of a microfluidic device testing the uniformity of the applied electric field in a 2-dimensional microfluidic chamber. "i" indicates the direction of the applied electric field. Experimental CCD images were taken of 0.1 µM free dye solution loaded into a microfluidic chamber. FIG. 15E shows that the electrokinetic movement of the dye through the microfluidic chamber was substantially uniform in the vertical direction. FIG. 15F shows that the electrokinetic movement of the dye through the microfluidic chamber was substantially uniform in the horizontal direction. The COMSOL simulations and experimental data both showed a well controlled, uniform electric field distribution in the vertical and horizontal dimensions within the microfluidic chamber. A uniform electric field distribution may facilitate precisely directing the sample and/or selected analytes of interest in multiple dimensions through the microfluidic device.

Figure 16:
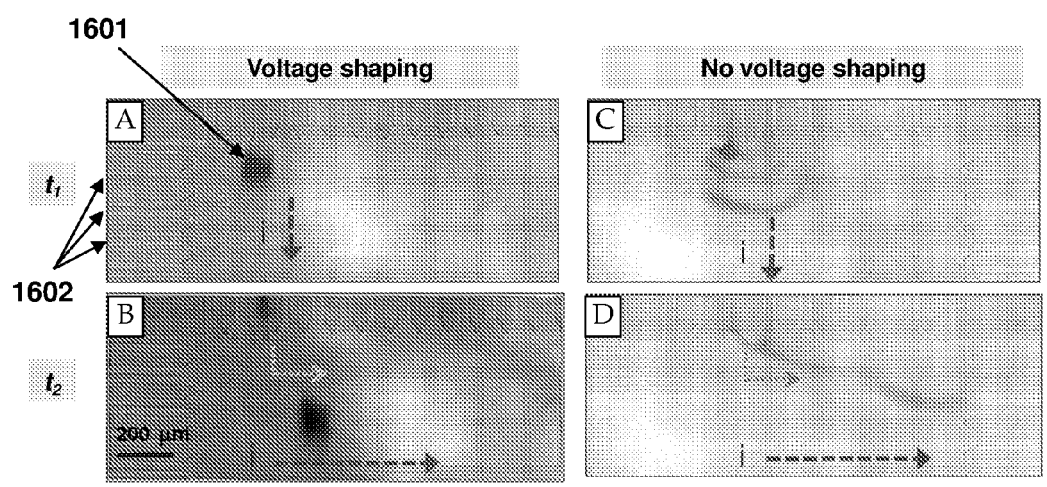
FIG. 16 shows CCD images of the electrokinetic movement of a sample through a microfluidic device with and without voltage shaping according to embodiments of the present disclosure.

FIG. 16 shows images of the electrokinetic movement of a sample 1601 through a microfluidic device with and without voltage shaping. Fluorescently labeled 0.1 µM BSA was injected into the microfluidic device and observed using CCD imaging. CCD images showed the band shape of the fluorescently labeled sample 1601 during the transfer step from the vertical to horizontal direction. The sample band shape was preserved without significant distortion after transfer by using shaping voltage. "i" indicates the direction of the applied electric field. In FIG. 16 (left), the sample 1601 maintained its original shape with substantially no distortion after entering into the separation chamber (see FIG. 16A) and substantially no distortion after being transferred to the second horizontal dimension (see FIG. 16B). FIGS. 16C and 16D indicated that without voltage shaping, the sample band shape becomes significantly distorted after entering into the separation chamber (see FIG. 16C) and after transferring to the second horizontal dimension (see FIG. 16D). Multiple side channels 1602 allow different samples, reagents, buffers, and the like, to be introduced into the microfluidic chamber. For example, additional samples, reagents, buffers, etc. may be introduced into the microfluidic chamber after separation of the analytes in the sample for subsequent sandwich antibody detection, enzymatic reaction, and the like.

Figure 18:
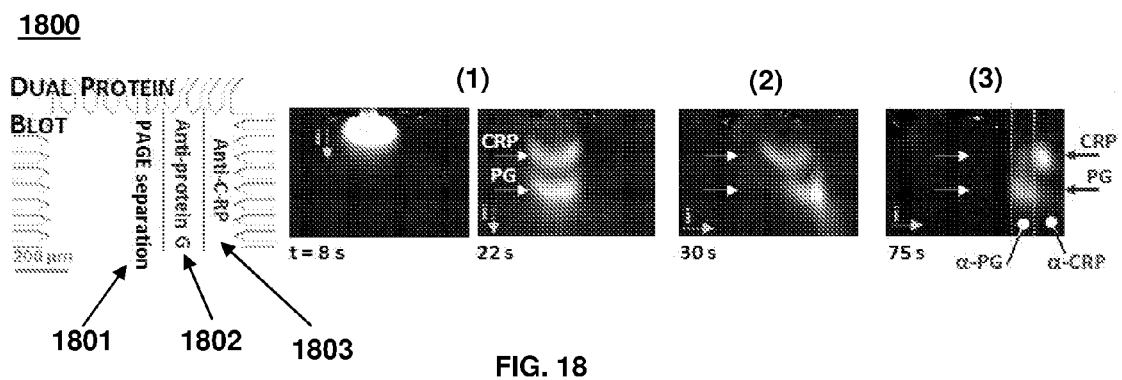
FIG. 18 shows images of the separation, transfer and detection of multiple analytes in a sample according to embodiments of the present disclosure.

FIG. 18 shows images of the separation, transfer and detection of multiple analytes in a sample. The microfluidic device 1800 included a microfluidic chamber (1 mm×1 mm) that contained a separation medium (6% total acrylamide) 1801 and two different binding media; a first binding medium (6% total acrylamide) 1802 that included binding members specific to PG, and a second binding medium (6% total acrylamide) 1803 that included binding members specific to CRP. The separation medium and binding media were formed by selective photopatterning using mask-based UV lithography of polyacrylamide gels. Selective photopatterning enabled the formation of an integrated medium in a microfluidic chamber, where the medium included distinct regions of different physical and functional properties for analyte separation (e.g., the separation medium) and antibody-based detection (e.g., the binding media).

In FIG. 18, a sample that included target proteins Protein G (PG) and C-Reactive Protein (CRP) was electrophoretically separated by directing the sample through a separation medium 1801 using an electric field strength of 150 V/cm (FIG. 18, step (1)). Baseline separation of PG and CRP was complete in about 20 sec. The separated target proteins PG and CRP were transferred to the binding media using a lateral electric field (50V/cm) (FIG. 18, step (2)). The separated sample band that included PG selectively bound to the binding medium that included binding members specific to PG (~80% capture efficiency), and the separated sample band that included CRP selectively bound to the binding medium that included binding members specific to CRP (~80% capture efficiency) (FIG. 18, step (3)). The separation, transfer and detection steps were performed within 90 seconds. With low cross-reactivity, each analyte was bound to antibody immobilized in their respective blotting regions.

Figure 19:
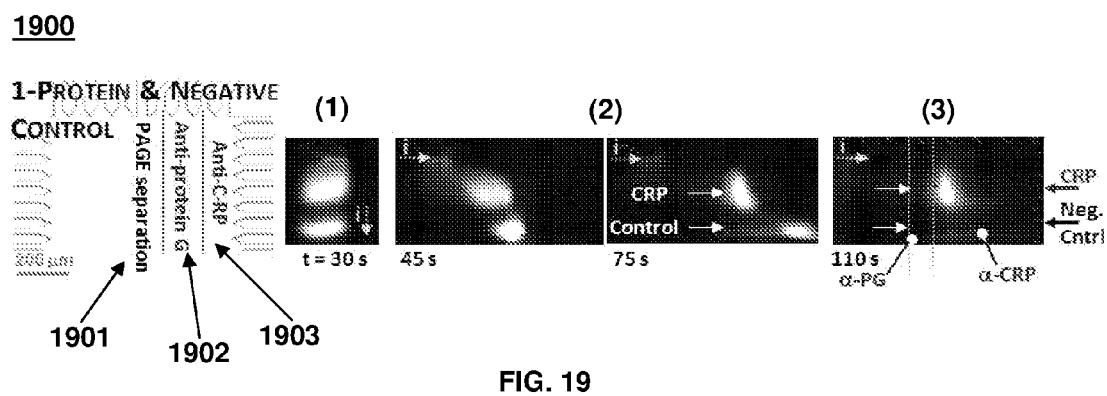
FIG. 19 shows images of the separation, transfer and detection of an analyte in a sample vs a negative control according to embodiments of the present disclosure.

FIG. 19 shows images of the separation, transfer and detection of an analyte in a sample vs a negative control. The microfluidic device 1900 included a microfluidic chamber (1 mm×1 mm) that contained a separation medium (6% total polyacrylamide) 1901 and two different binding media; a first binding medium (6% total polyacrylamide) 1902 that included binding members specific to PG, and a second binding medium (6% total polyacrylamide) 1903 that included binding members specific to CRP. A sample that included C-Reactive Protein (CRP) and a negative control (bovine serum albumin (BSA)) was electrophoretically separated by directing the sample through a separation medium 1901 using an electric field strength of 150 V/cm (FIG. 19, step (1)). Baseline separation of CRP and BSA was complete in 30 sec. The separated bands of CRP and BSA negative control were transferred to the binding media using a lateral electric field (50V/cm) (FIG. 19, step (2)). The separated sample band that included CRP selectively bound to the binding medium that included binding members specific to CRP (FIG. 19, step (2)). The separated sample band that included the BSA negative control did not selectively bind to either binding media and showed no detectable cross-reactivity or non-specific adsorption (FIG. 18, step (3)). The separation, transfer and detection steps were performed within 110 seconds.

Figure 20:
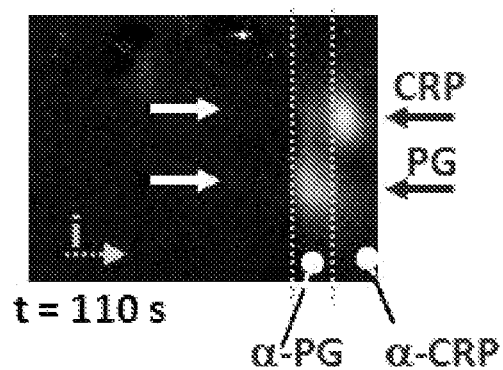
FIG. 20 shows an image of the multiplex detection of multiple analytes in a sample according to embodiments of the present disclosure.

FIG. 20 shows an image of the multiplex detection of multiple analytes in a sample. Following electrophoretic separation, target proteins Protein G (PG) and C-Reactive Protein (CRP) were selectively captured and detected at antibody functionalized binding media (see FIG. 18). Target proteins were retained in their respective binding media after exposure to a lateral electric field (>110 s at 50 V/cm). The results indicated that analytes remained specifically bound to the binding medium after exposure to an applied electric field for 110 sec or more.

Figure 21:
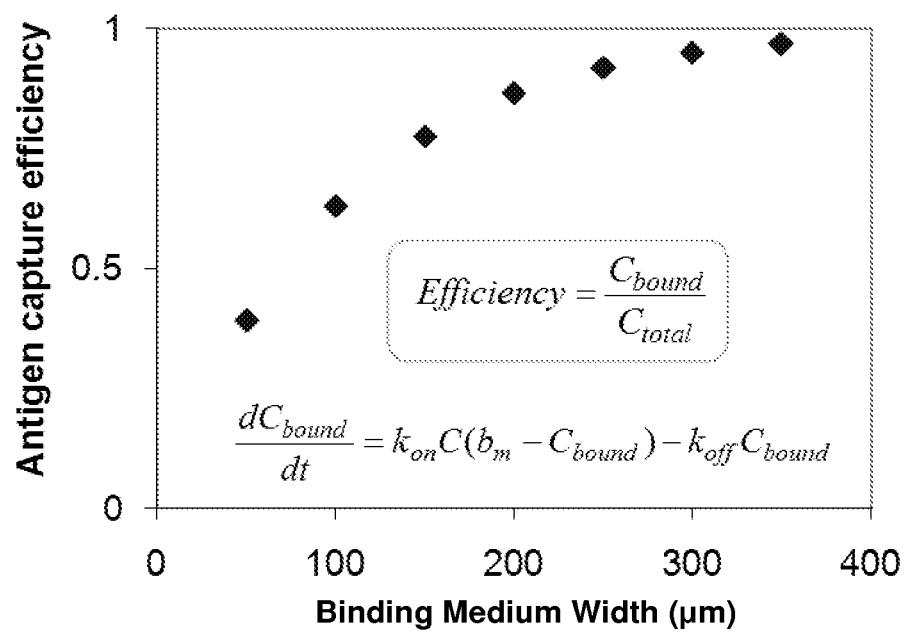
FIG. 21 shows a graph of antigen capture efficiency vs binding medium width (µm) according to embodiments of the present disclosure.

FIG. 21 shows a graph of antigen capture efficiency vs binding medium width (μm). Antigen capture efficiency was modeled as a function of design and operation parameters, assuming Langmuir binding kinetics. Modeling may facilitate optimization of the binding medium (e.g, binding medium width, binding member density, etc.) for microfluidic devices configured for multiplex analysis of multiple analytes in a sample.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A microfluidic device for detecting an analyte in a fluid sample, wherein the microfluidic device comprises a contiguous monolith comprising:

a separation medium having a separation flow path with a first directional axis; and a binding medium having a labeling flow path with a second directional axis, wherein the binding medium is in fluid communication with the separation medium, wherein the microfluidic device is configured to subject a sample to two or more directionally distinct flow fields coplanar with the separation medium.

2. The microfluidic device according to claim 1, wherein the two or more directionally distinct flow fields comprise two or more directionally distinct electric fields.

3. The microfluidic device according to claim 1, wherein the separation medium comprises a polymeric gel.

4. The microfluidic device according to claim 1, wherein the binding medium comprises a binding member stably associated with a support.

5. The microfluidic device according to claim 4, wherein the support comprises a membrane.

6. The microfluidic device according to claim 4, wherein the support comprises a polymeric gel.

7. The microfluidic device according to claim 4, wherein the binding member comprises a protein or a binding fragment thereof.

8. The microfluidic device according to claim 7, wherein the protein is an antibody.

9. The microfluidic device according to claim 1, wherein the analyte comprises a fluorescent label.

10. The microfluidic device according to claim 1, wherein the second directional axis is orthogonal to the first directional axis.

11. The microfluidic device according to claim 1, wherein the microfluidic device comprises a chamber containing the separation medium and the binding medium.

12. A method of detecting an analyte in a fluid sample, the method comprising:
  (a) introducing the fluid sample into a microfluidic device configured to subject a sample to two or more directionally distinct flow fields coplanar with a separation medium, wherein the microfluidic device comprises a contiguous monolith comprising:
    (i) the separation medium having a separation flow path with a first directional axis; and
    (ii) a binding medium having a labeling flow path with a second directional axis, wherein the binding medium is in fluid communication with the separation medium;
  (b) directing the sample through the separation medium to produce a separated sample; and
  (c) detecting the analyte in the separated sample.

13. A system for detecting an analyte in a fluid sample, the system comprising:
  (a) a microfluidic device configured to subject a sample to two or more directionally distinct flow fields coplanar with a separation medium, wherein the microfluidic device comprises a contiguous monolith comprising:
    (i) the separation medium having a separation flow path with a first directional axis; and
    (ii) a binding medium having a labeling flow path with a second directional axis, wherein the binding medium is in fluid communication with the separation medium; and
  (b) a detector.

14. The system according to claim 13, wherein the two or more directionally distinct flow fields comprise two or more directionally distinct electric fields.

15. The system according to claim 13, wherein the detector is a photomultiplier tube, a charge-coupled device, an intensified charge-coupled device, a complementary metal-oxide-semiconductor sensor, visual colorimetric readout, or a photodiode.

16. The system according to claim 13, further comprising microfluidic components configured to direct a fluid through the microfluidic device.

17. A kit comprising:
  (a) a microfluidic device configured to subject a sample to two or more directionally distinct flow fields coplanar with a separation medium, wherein the microfluidic device comprises a contiguous monolith comprising:
    (i) the separation medium having a separation flow path with a first directional axis; and
    (ii) a binding medium having a labeling flow path with a second directional axis, wherein the binding medium is in fluid communication with the separation medium; and
  (b) a buffer.

18. The kit according to claim 17, wherein the two or more directionally distinct flow fields comprise two or more directionally distinct electric fields.

19. The microfluidic device according to claim 1, wherein the separation medium is copolymerized to the binding medium.

20. The microfluidic device according to claim 1, wherein the microfluidic device comprises a chamber containing the contiguous monolith.

21. The microfluidic device according to claim 1, wherein the contiguous monolith comprises a contiguous polymeric gel monolith.

22. The microfluidic device according to claim 1, wherein the contiguous monolith comprises a loading medium in fluid communication with the separation medium and having a flow path in the same direction as the first directional axis.

23. The microfluidic device according to claim 1, further comprising a buffer in fluid communication with the separation medium and the binding medium.

24. The microfluidic device according to claim 23, wherein the buffer comprises an electrophoresis buffer.

25. The microfluidic device according to claim 1, wherein the separation medium and the binding medium are in direct physical contact with each other, such that the analyte can traverse directly from the separation medium to the binding medium.

26. The microfluidic device according to claim 1, wherein the polymeric gel is a cross-linked polymeric gel.

* * * * *